(12) United States Patent
Mosenia et al.

(10) Patent No.: US 10,652,237 B2
(45) Date of Patent: May 12, 2020

(54) CONTINUOUS AUTHENTICATION SYSTEM AND METHOD BASED ON BIOAURA

(71) Applicants: Arsalan Mosenia, Princeton, NJ (US); Susmita Sur-Kolay, Kolkata (IN); Anand Raghunathan, West Lafayette, IN (US); Niraj K. Jha, Princeton, NJ (US)

(72) Inventors: Arsalan Mosenia, Princeton, NJ (US); Susmita Sur-Kolay, Kolkata (IN); Anand Raghunathan, West Lafayette, IN (US); Niraj K. Jha, Princeton, NJ (US)

(73) Assignees: THE TRUSTEES OF PRINCETON UNIVERSITY, Princeton, NJ (US); INDIAN STATISTICAL INSTITUTE, Kolkata (IN); PURDUE RESEARCH FOUNDATION, West Lafayette, IN (US)

( * ) Notice: Subject to any disclaimer, the term of this patent is extended or adjusted under 35 U.S.C. 154(b) by 165 days.

(21) Appl. No.: 15/425,440

(22) Filed: Feb. 6, 2017

(65) Prior Publication Data
US 2017/0230360 A1    Aug. 10, 2017

Related U.S. Application Data

(60) Provisional application No. 62/291,877, filed on Feb. 5, 2016.

(51) Int. Cl.
*H04L 29/06* (2006.01)
*A61B 5/117* (2016.01)
(Continued)

(52) U.S. Cl.
CPC .......... *H04L 63/0861* (2013.01); *A61B 5/117* (2013.01); *G06F 21/32* (2013.01);
(Continued)

(58) Field of Classification Search
CPC .... H04L 63/0861; G06F 21/32; H04W 12/06; A61B 5/117; A61B 5/024; A61B 5/0816;
(Continued)

(56) References Cited

U.S. PATENT DOCUMENTS 7,957,722 B2 *   6/2011   Ritter ............... G06F 21/35
                                                       455/410
9,843,596 B1 * 12/2017   Averbuch ......... H04L 63/1416
(Continued)

OTHER PUBLICATIONS

P. S. Teh, A. B. J. Teoh, and S. Yue. "A survey of keystroke dynamics biometrics." The Scientific World Journal, vol. 2013, 2013.
(Continued)

*Primary Examiner* — Meng Li
(74) *Attorney, Agent, or Firm* — Meagher Emanuel Laks Goldberg & Liao, LLP

(57) ABSTRACT

A user authentication system for an electronic device for use with a plurality of wireless wearable medical sensors (WMSs) and a wireless base station that receives a biomedical data stream (biostream) from each WMS. The system includes a BioAura engine located on a server, the server has a wireless transmitter/receiver with receive buffers that store the plurality of biostreams, the BioAura engine has a look up stage and a classifier, the classifier generates an authentication output based on the plurality of biostreams, the authentication output authenticates the user's access to the electronic device. The wireless base station has a transmitter/receiver having receive buffers that store the biomedical data from each WMS, the wireless base station has a communication engine that retrieves the biostream from each WMS and transmits the plurality of biostreams to the server.

20 Claims, 10 Drawing Sheets

(51) Int. Cl.
*H04W 12/06* (2009.01)
*G06F 21/32* (2013.01)
*G16H 10/60* (2018.01)
*G16H 40/67* (2018.01)
*G16H 40/63* (2018.01)
*A61B 5/01* (2006.01)
*A61B 5/021* (2006.01)
*A61B 5/08* (2006.01)
*A61B 5/024* (2006.01)
*A61B 5/145* (2006.01)

(52) U.S. Cl.
CPC .............. *G16H 10/60* (2018.01); *G16H 40/63* (2018.01); *G16H 40/67* (2018.01); *H04W 12/06* (2013.01); *A61B 5/01* (2013.01); *A61B 5/021* (2013.01); *A61B 5/024* (2013.01); *A61B 5/0816* (2013.01); *A61B 5/14542* (2013.01)

(58) Field of Classification Search
CPC ....... A61B 5/14552; A61B 5/021; A61B 5/01; A61B 5/14542; G16H 10/60; G16H 40/67; G16H 40/63
See application file for complete search history.

(56) References Cited

U.S. PATENT DOCUMENTS

| | | | | |
|---|---|---|---|---|
| 2010/0049005 | A1* | 2/2010 | Espina Perez | A61B 5/0002 600/300 |
| 2014/0089672 | A1* | 3/2014 | Luna | H04L 9/3231 713/186 |
| 2016/0183812 | A1* | 6/2016 | Zhang | A61B 5/7246 600/301 |

OTHER PUBLICATIONS

N. K. Ratha, J. H. Connell, and R. M. Bolle, "Enhancing security and privacy in biometrics-based authentication systems," IBM Systems Journal, vol. 40, No. 3, pp. 614-634, 2001.
A. J. Aviv, K. Gibson, E. Mossop, M. Blaze, and J. M. Smith, "Smudge attacks on smartphone touch screens," in Proc. USENIX Wkshp. Offensive Technologies, vol. 10, pp. 1-7, 2010.
C. Ma, D. Wang, and S. Zhao, "Security flaws in two improved remote user authentication schemes using smart cards," Int. J. Communication Systems, vol. 27, No. 10, pp. 2215-2227, 2014.
D. He and S. Wu, "Security flaws in a smart card based authentication scheme for multi-server environment," Wireless Personal Communications, vol. 70, No. 1, pp. 323-329, 2013.
N. L. Clarke, S. M. Furnell, and P. L. Reynolds, "Biometric authentication for mobile devices," in Proc. Third Australian Information Warfare and Security Conference, pp. 61-69, 2002.
S. Egelman, S. Jain, R. S. Portnoff, K. Liao, S. Consolvo, and D.Wagner, "Are you ready to lock?" in Proc. ACM Conf. Computer and Communications Security, pp. 750-761, 2014.
G. K. O. Michael, T. Connie, and A. B. J. Teoh, "Touch-less palm print biometrics: Novel design and implementation," Image and Vision Computing, vol. 26, No. 12, pp. 1551-1560, 2008.
K. Niinuma, U. Park, and A. K. Jain, "Soft biometric traits for continuous user authentication," IEEE Trans. Information Forensics and Security, vol. 5, No. 4, pp. 771-780, 2010.
P. Bours, "Continuous keystroke dynamics: A different perspective towards biometric evaluation," Information Security Technical Report, vol. 17, No. 1, pp. 36-43, 2012.
S. Mondal and P. Bours, "Continuous authentication using mouse dynamics," in Proc. IEEE Int. Conf. Biometrics Special Interest Group, pp. 1-12, 2013.
A. Pantelopoulos and N. G. Bourbakis, "A survey on wearable sensor based systems for health monitoring and prognosis," IEEE Trans. Systems, Man, and Cybernetics, vol. 40, No. 1, pp. 1-12, 2010.

J. Anliker, J. Ward, P. Lukowicz, G. Tr' oster, F. Dolveck, M. Baer, F. Keita, E. B. Schenker, F. Catarsi, and L. Coluccini, "AMON: A wearable multiparameter medical monitoring and alert system," IEEE Trans. Information Technology in Biomedicine, vol. 8, No. 4,pp. 415-427, 2004.
F. Xu, Z. Qin, C. C. Tan, B. Wang, and Q. Li, "IMDGuard: Securing implantable medical devices with the external wearable guardian," in Proc. IEEE Infocom, pp. 1862-1870, 2011.
"Growth trends, consumer attitudes, and why smartwatches will dominate," http://www.businessinsider.com/the-wearable-computing-marketreport—Oct. 2014, published Oct. 2014.
M. Mihajlov and B. Jerman-Blažič, "On designing usable and secure recognition-based graphical authentication mechanisms," Interacting with Computers, vol. 23, No. 6, pp. 582- 593, 2011.
J. Roth, X. Liu, and D. Metaxas, "On continuous user authentication via typing behavior," IEEE Trans. Image Processing, vol. 23, No. 10, pp. 4611-4624, 2014.
K. Revett, H. Jahankhani, S. T. de Magalhães, and H. M. Santos, "A survey of user authentication based on mouse dynamics," in Global ESecurity. Springer, pp. 210-219, 2008.
S. P. Banerjee and D. L Woodard, "Biometric authentication and identification using keystroke dynamics: A survey," J. Pattern Recognition Research, vol. 7, No. 1, pp. 116-139, 2012.
S.M. Furnell, P. Dowland, H. Illingworth, and P. L. Reynolds, "Authentication and supervision: A survey of user attitudes," Computers & Security, vol. 19, No. 6, pp. 529-539, 2000.
M. Frank, R. Biedert, E.-D. Ma, I. Martinovic, and D. Song, "Touchalytics: On the applicability of touchscreen input as a behavioral biometric for continuous authentication," IEEE Trans. Information Forensics and Security, vol. 8, No. 1, pp. 136-148, 2013.
W. Lee and R. B. Lee, "Multi-sensor authentication to improve smartphone security," in Proc. Conf. Information Systems Security and Privacy, 2015.
D. Anguita, A. Ghio, L. Oneto, X. Parra, and J. L. Reyes-Ortiz, "Human activity recognition on smartphones using a multiclass hardware-friendly support vector machine," in Proc. Ambient Assisted Living and Home Care, pp. 216-223, 2012.
H. G. Kayacik, M. Just, L. Baillie, D. Aspinall, and N. Micallef, "Data driven authentication: On the effectiveness of user behaviour modelling with mobile device sensors," arXiv preprint arXiv: 1410.7743, 2014.
L. Li, X. Zhao, and G. Xue, "Unobservable re-authentication for smartphones," in Proc. Network and Distributed System Security, 2013.
E. B. Mazomenos, D. Biswas, A. Acharyya, T. Chen, K. Maharatna, J. Rosengarten, J. Morgan, and N. Curzen, "A low-complexity ECG feature extraction algorithm for mobile healthcare applications," IEEE J. Biomedical and Health Informatics, vol. 17, No. 2, pp. 459-469, 2013.
P. R. Rijnbeek, J. A. Kors, and M. Witsenburg, "Minimum bandwidth requirements for recording of pediatric electrocardiograms," Circulation, vol. 104, No. 25, pp. 3087-3090, 2001.
J. A. Suykens and J. Vandewalle, "Least squares support vector machine classifiers," Neural Processing Letters, vol. 9, No. 3, pp. 293-300, 1999.
Y. Freund, R. Schapire, and N. Abe, "A short introduction to boosting," J. Japanese Society for Artificial Intelligence, vol. 14, No. 771-780, p. 1612, 1999.
M. Saeed, M. Villarroel, A. T. Reisner, G. Clifford, L.-W. Lehman, G. Moody, T. Heldt, T. H. Kyaw, B. Moody, and R. G. Mark, "Multiparameter intelligent monitoring in intensive care II (MIMIC-II): A public-access intensive care unit database," Critical Care Medicine, vol. 39, No. 5, p. 952, 2011.
S. Arlot and A. Celisse, "A survey of cross-validation procedures for model selection," Statistics Surveys, vol. 4, pp. 40-79, 2010.
D. Mease and A. Wyner, "Evidence contrary to the statistical view of boosting," J. Machine Learning Research, vol. 9, pp. 131-156, 2008.
I. Deutschmann, P. Nordstrom, and L. Nilsson, "Continuous authentication using behavioral biometrics," IEEE IT Professional, vol. 15, No. 4, pp. 12-15, 2013.
"HackRF One." https://greatscott.gadgets.com/hackrf/, accessed: Oct. 1, 2015.

(56) References Cited

OTHER PUBLICATIONS

J. Daemen and V. Rijmen. "The Design of Rijndael: AES—The Advanced Encryption Standard." Springer Science and Business Media. 2013.

C. Abad. "The economy of phishing: A survey of the operations of the phishing market." First Monday. vol. 10. No. 9. 2005.

R. Dhamija, .L D. Tygar. and M. Hearst. "Why phishing works", in Proc. ACM Conf Human Factors in Computing Systems. pp. 581-590, 2006.

B. Biggio. B. Nelson. and P. Laskov. "Poisoning attacks against support vector machines," arXiv preprint arXiv: 1206.6389, 2012.

M. Mozaffari-Kermani, S. Sur-Kolay, A. Raghunathan, and N. K. Jha, "Systematic poisoning attacks on and defenses for machine learning in healthcare" IEEE J Biomedical and Health Informatics, vol. 19, No. 6, pp. 1893-1905. 2015.

\* cited by examiner

CONTINUOUS AUTHENTICATION SYSTEM AND METHOD BASED ON BIOAURA

CROSS-REFERENCE TO PRIOR FILED APPLICATIONS

This application claims priority to U.S. provisional application 62/291,877, filed Feb. 5, 2016, which is incorporated herein in its entirety.

STATEMENT REGARDING FEDERALLY SPONSORED RESEARCH OR DEVELOPMENT

This invention was made with government support under Grant CNS-1219570 awarded by the National Science Foundation. The government has certain rights in the invention.

FIELD OF THE INVENTION

The present disclosure generally relates to the field of authentication systems and in more particular, authentication systems based on biomedical data streams.

BACKGROUND

Authentication refers to the process of verifying a user based on certain credentials, before granting access to a secure system, resource, or area. Vulnerabilities in an authentication system may be exploited by adversaries, leading to leakage of confidential data (e.g., encryption keys), compromised integrity, and loss of privacy. The need for an authentication mechanism is not limited to logging in to computers. It is also needed to protect restricted physical spaces (e.g., datacenters) and secure software (e.g., e-commerce) applications.

Traditionally, authentication is only performed when the user initially interacts with the system. In these scenarios, the user faces a knowledge-based authentication challenge (e.g., a password inquiry), and the user is authenticated only if he offers the correct answer (e.g., the password).

Although one-time authentication has been the dominant authentication mechanism for decades, several issues spanning user inconvenience to security flaws have been investigated by researchers. For example, the user has to focus on several authentication steps when he tries to unlock a smart phone, which utilizes a password/pattern-based authentication method. This may lead to safety risks (e.g., distraction when the user is driving). A serious security flaw of one-time authentication is its inability to detect intruders after initial authentication has been performed. For example, an unauthorized user can access private resources of the initial user if he leaves his authenticated device to take a break, or forgets to log out.

The above concerns have led to investigations of continuous authentication mechanisms, which frequently monitor the user's interactions with the device even after the initial login to ensure that the initially-authenticated user is still the one using the device. Initial efforts in this direction were based on simple security policies that lock the user's device after a period of inactivity, and ask the user to re-enter the password. However, such schemes may be annoying and expose a window of vulnerability, leaving much room for improvement.

SUMMARY OF THE INVENTION

A user authentication system for an electronic device is disclosed. The system is used with a plurality of wireless wearable medical sensors (WMSs) and a wireless base station configured to receive a biomedical data stream (biostream) from each of the plurality of WMSs. The system includes a BioAura engine located on a server, the server being configured with a wireless transmitter/receiver having receive buffers configured to store the plurality of biostreams, the biostream from a single WMS lacking the discriminatory power to distinguish the user, the BioAura engine having a look up stage and a classifier, the classifier being configured to generate an authentication output based on the plurality of biostreams, the authentication output being configured to authenticate the user's access to the electronic device. The wireless base station is configured with a wireless transmitter/receiver having receive buffers configured to store the biomedical data from each WMS, the wireless base station having a communication engine configured to retrieve the biostream from each WMS and transmit the plurality of biostreams to the server.

The plurality of biostreams may be selected from the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2) and Respiratory rate (RESP). The plurality of biostreams may include at least three of the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2) and Respiratory rate (RESP). The plurality of biostreams may include the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2) and Respiratory rate (RESP). It should be understood that the plurality of biostreams may include 4 or 5 or 6 or 7 or 8 or all 9 of the above disclosed biostreams depending on the desired target accuracy level.

The plurality of biostreams may be selected based on a target accuracy level. The BioAura engine may be operated continuously, generating the authentication output on a periodic or a-periodic basis. The communication engine may be configured to process the biostreams to reduce the bandwidth needed to transmit the biostream to the BioAura engine. The base station may be a smartphone. The electronic device may be at least one of a tablet and a smart lock. The classifier may be implemented using Support one of Vector Machine (SVM) and Adaptive Boosting (AdaBoost).

A user authentication system for a computing device is also disclosed. The system is used with a plurality of wireless wearable medical sensors (WMSs) and a wireless base station configured to receive a biomedical data stream (biostream) from each of the plurality of WMSs. The system includes a BioAura engine located on the computing device, the computing device being configured with a wireless transmitter/receiver having receive buffers configured to store the plurality of biostreams, the biostream from a single WMS lacking the discriminatory power to distinguish the user, the BioAura engine having a look up stage and a classifier, the classifier being configured to generate an authentication output based on the plurality of biostreams, the authentication output being configured to authenticate the user's access to the computing device. The wireless base station is configured with a wireless transmitter/receiver having receive buffers configured to store the biomedical data from each WMS, the wireless base station having a communication engine configured to retrieve the biostream from each WMS and transmit the plurality of biostreams to the computing device.

The plurality of biostreams may be selected from the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2) and Respiratory rate (RESP). The plurality of biostreams may include at least three of the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2) and Respiratory rate (RESP). The plurality of biostreams may include the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2) and Respiratory rate (RESP). It should be understood that the plurality of biostreams may include 4 or 5 or 6 or 7 or 8 or all 9 of the above disclosed biostreams depending on the desired target accuracy level.

The plurality of biostreams may be selected based on a target accuracy level. The communication engine may be configured to process the biostreams to reduce the bandwidth needed to transmit the biostream to the computing device. The computing device may be a personal computer. The BioAura engine may be operated continuously, generating the authentication output on a periodic or a-periodic basis. The classifier may be implemented using Support one of Vector Machine (SVM) and Adaptive Boosting (AdaBoost).

A method of authenticating a user authentication of an electronic device is disclosed. The method is used with a plurality of wireless wearable medical sensors (WMSs) and a wireless base station configured to receive a biomedical data stream (biostream) from each of the plurality of WMSs. The method includes providing a BioAura engine located on a server, the server being configured with a wireless transmitter/receiver having receive buffers configured to store the plurality of biostreams, the biostream from a single WMS lacking the discriminatory power to distinguish the user, the BioAura engine having a look up stage and a classifier, the classifier being configured to generate an authentication output based on the plurality of biostreams, the authentication output being configured to authenticate the user's access to the electronic device. The wireless base station is configured with a wireless transmitter/receiver having receive buffers configured to store the biomedical data from each WMS, the wireless base station having a communication engine configured to retrieve the biostream from each WMS and transmit the plurality of biostreams to the server.

A method of authenticating a user of a computing device is also disclosed. The method is used with a plurality of wireless wearable medical sensors (WMSs) and a wireless base station configured to receive a biomedical data stream (biostream) from each of the plurality of WMSs. The method includes providing a BioAura engine located on the computing device, the computing device being configured with a wireless transmitter/receiver having receive buffers configured to store the plurality of biostreams, the biostream from a single WMS lacking the discriminatory power to distinguish the user, the BioAura engine having a look up stage and a classifier, the classifier being configured to generate an authentication output based on the plurality of biostreams, the authentication output being configured to authenticate the user's access to the computing device. The wireless base station is configured with a wireless transmitter/receiver having receive buffers configured to store the biomedical data from each WMS, the wireless base station having a communication engine configured to retrieve the biostream from each WMS and transmit the plurality of biostreams to the computing device.

BRIEF DESCRIPTION OF THE FIGURES

To facilitate understanding, identical reference numerals have been used, where possible, to designate identical elements that are common to the figures.

DETAILED DESCRIPTION

Figure 1:
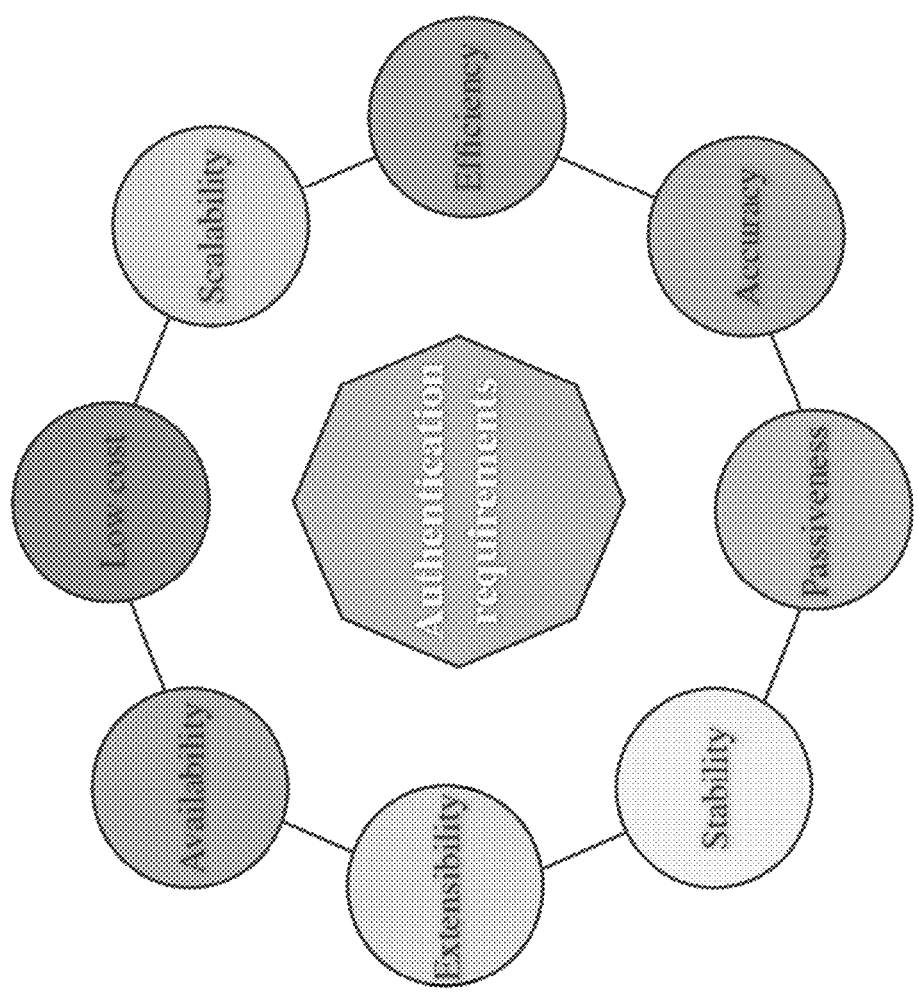
FIG. 1 is a block diagram with "design-octagon" including eight design requirements that a continuous authentication mechanism must satisfy.

Recently, wearable medical sensors (WMSs) have drawn a lot of attention from the research community. WMSs measure physiological data (e.g., heart rate, blood pressure, and body temperature). A recent report by Business Insider claims that 33 million wearable health monitoring devices have been sold in 2015. It forecasts that this number will reach 148 million by 2019. In the years after that, such usage is expected to explode further. If such physiological data will be collected anyway for health monitoring purposes, it is worthwhile to investigate if they also have authentication value. The use of continuously-collected biomedical data for user verification and identification is promising for three main reasons. First, data collection does not require any extra device not already on the body. Second, the data is collected transparently to the user. Third, unlike traditional biometrics/behaviometrics (e.g., face feature and keyboard pattern) information that may frequently become unavailable, the stream of biomedical data can be assumed to be always available when the person is wearing WMSs.

Disclosed herein is a system for Continuous Authentication Based on BioAura (CABA). A novel continuous authentication system that is inspired by and leverages the emergence of sensors for pervasive and continuous health monitoring. In this disclosure the term BioAura refers to an ensemble of biomedical data streams that can be collected continuously and non-invasively using wearable medical devices. Each biomedical data stream in isolation may not be highly discriminative. It is demonstrated herein that a collection of such biomedical data, along with robust machine learning, can provide high accuracy levels. The feasibility of CABA is demonstrated through analysis of traces from the MIMIC-II dataset. Various applications of CABA are also disclosed herein. The system may be extended to user identification and adaptive access control authorization. Possible threats to the CABA system and suggested countermeasures are also disclosed.

The CABA system is a novel transparent continuous authentication system based on a new class of traits called "BioAura." The term "aura" is traditionally defined as the energy field around a person. Analogously, the term "BioAura" as used herein defines the biological field around a person, manifested as a set of biomedical data streams (Biostreams in short). A Biostream is defined as a sequence of biomedical data samples that are continuously gathered by a WMS for medical diagnosis and therapeutic purposes. The most important difference between a Biostream and a biometric trait is that a single Biostream alone does not have enough discriminatory power to distinguish individuals. Thus, an authentication decision based on a single Biostream (e.g., body temperature or blood pressure) might only be slightly discriminative. However, when multiple Biostreams are combined into a BioAura, it leads to a powerful continuous authentication scheme. Disclosed herein is a comprehensive list of criteria that should be satisfied by authentication mechanisms. Also disclosed herein is an analysis of how the CABA system meets all these requirements, whereas biometrics/behaviometrics-based continuous authentication mechanisms do not.

Desirable authentication requirements and advantages of CABA

A systematic comparison between CABA and previously-proposed continuous authentication system is disclosed. A list of desirable requirements that an authentication mechanism must satisfy is provided. Then, the CABA system is compared with biometrics- and behaviometrics-based continuous authentication mechanisms based on these requirements.

Design-Octagon

Currently, there is no standard list of design requirements that a continuous authentication mechanism must satisfy. FIG. 1 is a block diagram with "design-octagon" including eight design requirements that a continuous authentication mechanism must satisfy. The individual design requirements are discussed in detail below.

1. Passiveness: A user-friendly system must not require frequent user involvement. For example, if the authentication mechanism asks the user to re-enter his credentials too often, it may be quite annoying to the user.

2. Availability: The system should provide a reliable authentication mechanism at all time instances. Lack of continuous availability is a significant drawback of several previously-proposed continuous authentication mechanisms—they may often fail due to a lack of sufficient information. For instance, a face recognition system, which fails to capture the user's face when he is moving, may unintentionally reject a legitimate user.

3. High accuracy: One of the most important requirement of every authentication system is high accuracy. The system should be able to confidently and accurately distinguish legitimate users from impostors, and reject impostors' requests.

4. Scalability: The system should be able to handle a growing amount of work when the number of users increases. In particular, its time and space complexity should increase modestly with an increase in the number of users.

5. Efficiency: A short response time (i.e., the time required to capture a test sample, process it, and provide a decision) is very desirable from both user convenience and security perspectives. While it is obviously desirable for the system to quickly authenticate a legitimate user and reject an impostor, security may also suffer if there is an appreciable delay. For example, if authorization takes five minutes, an impostor may be able to control the system and access restricted resources in that five-minute timeframe, while the system is still processing.

6. Low cost: Cost is another important factor in authentication systems used in low-security environments (e.g., in personal computers). In such environments, the cost of adding or modifying the authentication mechanism should ideally be negligible. Thus, mechanisms that do not need extra peripherals (e.g., retina scanners) would be generally preferred. However, for high-security environments (e.g., military bases), expensive authentication mechanisms could be deployed.

7. Stability: Any trait that is recorded for processing for authentication purposes must ideally have only slight changes or maintain its pattern over a certain time period.

8. Extensibility: The authentication system should be able to function on a wide variety of devices regardless of underlying hardware. Ideally, the system should not require dedicated hardware. Its design should take a large set of applications into consideration. It should be extensible to different environments with a minimum level of effort.

Advantages of the CABA System

In this subsection, the CABA system is compared to previously-proposed schemes (biometrics- and behaviometrics-based). Table I highlights the significant advantages of the CABA system and describes how it addresses the different requirements of the Design-octagon. Table II compares the CABA system to continuous biometrics- and behaviometrics-based authentication mechanisms. Although a detailed discussion of the advantages and disadvantages of previously-proposed schemes is beyond the scope of this disclosure paper, several scientific and engineering publications in the area of authentication were reviewed. The summarized advantages and weaknesses of biometrics- and behaviometrics-based mechanisms are shown in Table II.

TABLE I

Characteristics of the CABA system

| Requirement | Description |
| --- | --- |
| Passiveness | Ensured by using WMSs that minimize user's involvement. |
| Availability | Achieved by using continuously-monitored Biostreams. |
| Accuracy | Demonstrated below. |
| Scalability | As shown below, an increase in the number of users can be easily handled in this system. |
| Efficiency | Authentication can be done in a few milliseconds as discussed below. |
| Low cost | Use of already-deployed WMSs ensures that added cost is minimal. |
| Stability | High accuracy over different timeframes demonstrates that the collected data maintain their pattern over time. |

TABLE I-continued

Characteristics of the CABA system

| Requirement | Description |
| --- | --- |
| Extensibility | Unlike many biometric- and behaviometric-based schemes, CABA does not rely on authentication-specific components. |

TABLE II

Comparison of different continuous authentication mechanisms

| Mechanism | Passiveness | Availability | Accuracy | Scalability | Efficiency | Low cost | Stability | Extensibility |
| --- | --- | --- | --- | --- | --- | --- | --- | --- |
| Biometrics-based | − | − | + | + | + | + | + | − |
| Behaviometrics-based | + | − | + | + | + | + | + | − |
| CABA | + | + | + | + | + | + | + | + |

Since several of the previously-proposed methods fail to address passiveness, availability, and extensibility, we next elaborate how the CABA system ensures all of these.

Passiveness: In the CABA system, passiveness is addressed through the use of WMSs. These are small and compact sensors that are specifically designed to take the passiveness requirement into account, since continuous health monitoring needs to minimize user involvement. Thus, passiveness is not only a very desirable requirement for continuous authentication, but also a significant consideration in designing WMSs. Unfortunately, major biometrics-based mechanisms (e.g., fingerprint-based) do not provide a high level of passiveness.

Availability: Use of WMSs as capture devices also ensures a continuous stream of information since this is also required for continuous health monitoring. However, neither biometrics nor behaviometrics guarantees availability. For example, keyboard/mouse-based continuous authentication mechanisms fail when the user stops using the dedicated peripherals.

Extensibility: the CABA system can be implemented with a general-purpose computing unit, which collects the Biostreams, with sufficient memory capacity and computation power. Unfortunately, neither biometrics- nor behaviometrics-based mechanisms provide significant extensibility. For example, the nature of keyboard/mouse-based authentication schemes inherently limits their applications, i.e., they can only be used for implementing an authentication mechanism in a system that has a keyboard or a mouse.

The CABA system can also be used as a stand-alone one-time authentication system or as a complement to a knowledge-based authentication mechanism that provides one-time authentication. Although continuous authentication methods have begun to deal with several concerns (e.g., the possibility of stolen or forgotten passwords), traditional mechanisms still dominate current technologies, and in some scenarios, they may be intentionally preferred. Several such scenarios are discussed below.

Battery-powered devices: Incurring overheads of continuous authentication on a battery-powered device may drain its battery quickly, and lead to user inconvenience.

Low-security environment: Continuous authentication may not be required in a low-security environment (e.g., a common room in an apartment).

Intentionally-shared resources: A user might want to intentionally authorize a group of users to access some specific locations or resources. For example, consider a user who uses a lock automation system, which grants access to him when he approaches the door of his house. He may want to open the door for his guests and leave the house to go shopping. A continuous authentication system that requires the presence of the targeted person may be bothersome in this scenario.

Generally, a continuous authentication mechanism that has high accuracy and a short response time may be able to provide stand-alone one-time authentication or complement a traditional authentication mechanism (whose decision is only considered at the time of initial login). The CABA system can provide an accurate decision within a few milliseconds and, hence, is also useful in situations where one-time authentication is preferred.

Design Considerations

In order to describe how the CABA system functions, we first need to answer three fundamental design and implementation questions:

1. How can the Biostreams that constitute the BioAura be collected?
2. How can the collected Biostreams be transmitted to the authentication system?
3. Which Biostreams constitute the BioAura?

The in-depth answers to each question are set out below.

Data Collection

Figure 2:
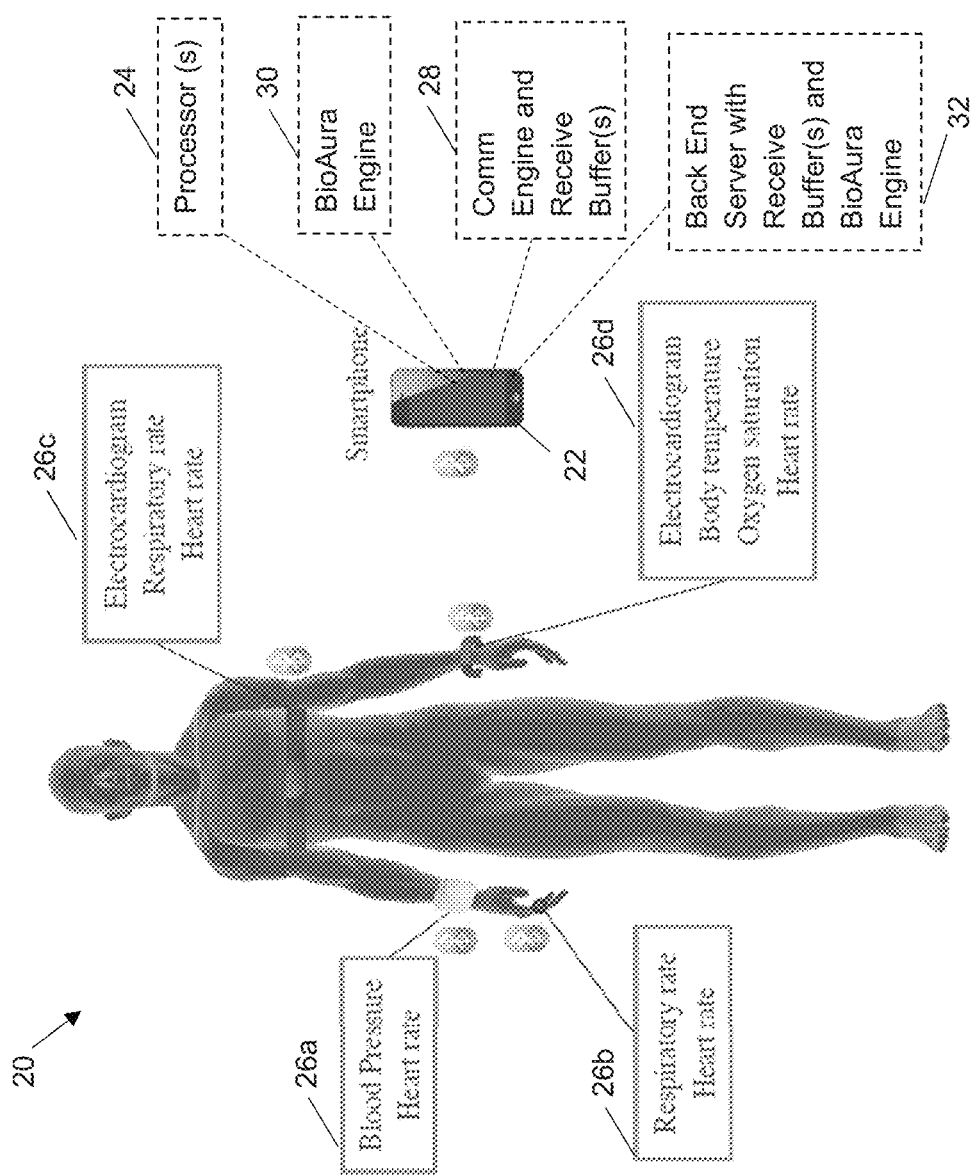
FIG. 2 is a block diagram of a CABA system.

Each Biostream is continuously and noninvasively captured by a corresponding WMS. The use of WMSs in conjunction with mobile devices like smartphones is revolutionizing healthcare systems by offering the possibility of inexpensive continuous health monitoring. The most widely-used scheme for continuous health monitoring consists of two main classes of components: (i) WMSs and (ii) a base station. The base station may range from smart phones to specialized wireless computing devices, known as health hubs. All WMSs transmit their data to the base station either for further processing or long-term storage. In recent years, smart phones have become the dominant base station since they are powerful and ubiquitous. FIG. 2 is a block diagram of a CABA system 20. This example is a simple continuous health monitoring system that includes several small lightweight WMSs 26a-26d, which transmit their biomedical data to the base station 22, e.g., a smart phone. Communications of data from the WMSs to the base station is typically accomplished via a wireless communication technique. In the examples below base station and back end servers are configured with Bluetooth transmitter/receivers (Bluetooth communication link) for wireless communication of the biomedical data. It should be understood that other wireless communication techniques may be used without departing from the scope of this disclosure. It should also be understood that the base station 22 includes at least one processor 24. The base station 22 also a wireless receiver, e.g., Bluetooth, with one more receive buffers 28 and from which the biomedical data is retrieved after it is received from the various WMSs. The base station 22 also includes a communication engine (as shown my block 28) configured to retrieve the biomedical data from the receive buffers. The communication engine may forward the biomedical data to the BioAura Engine 30 for processing of the biomedical data collected from the WMSs. In the alternative the communication engine may perform some signal processing on the biomedical data or simply re-transmit the raw biomedical data to a more powerful back-end server 32. The back-end server 32 is configured with a wireless receiver, e.g., Bluetooth, with one or more receive buffers to store the biomedical data and a BioAura Engine 30 for processing the biomedical data retrieved from the receive buffers.

Data Transmission

In a prototype implementation, it is assumed that the biomedical data is collected from the WMSs by a smartphone (e.g., base station 22) and transmitted to the authentication system (e.g., back end server 30) by the smartphone. This assumption is made for three main reasons. First, as mentioned earlier, recent technological advances have made the smartphone a promising candidate for use as a base station in continuous health monitoring. Second, its energy capacity is less limited relative to WMSs and the required biomedical data can be collected from the WMSs with a negligible energy overhead in the smartphone. Third, a smartphone can support secure communication links that can prevent several potential attacks against the system.

Smartphones can be integrated into the CABA system in two different ways: (i) they can simply retransmit the raw data, or (ii) they can perform simple preprocessing and only extract values of some important features from the data, and transmit those values. Each of these approaches has its own advantages. In the first approach, the back-end server can perform sophisticated feature extraction from the raw data before incorporating them in a model. This provides more flexibility in feature extraction. In the second approach, the amount of data can be minimized or reduced prior to transmission. This reduces the power consumed in data transmission. In one embodiment we assume that the smartphone first performs a very simple feature extraction function that computes the average value of the samples in each Biostream over the last one-minute timeframe of data. Afterwards, the base station or smartphone transmits only a feature vector that contains these average values. It should be understood that the various Biostreams may be processed in a variety of ways to reduce the transmission bandwidth required. It should also be understood that the Biostream data may be transmitted to/from the base station periodically or a-periodically with a wide variety of intervals between individual transmissions.

BioAura

The next section addresses which Biostreams constitute the BioAura. From a continuous health monitoring perspective, the WMSs that produce the Biostreams must satisfy two requirements: (i) they must need minimum user involvement, and (ii) the biomedical signals gathered by them should be essential for routine health monitoring.

Table III shows the most commonly-used Biostreams, their abbreviations or notations used in the medical literature, and their units. In this disclosure we exclude the first three Biostreams from the proposed BioAura, and include the other nine. Next, we discuss why the three Biostreams are excluded.

TABLE III

Biostreams, their abbreviations/notations, and units

| Biostream | Abbreviations/Notations | Unit |
| --- | --- | --- |
| Electroencephalogram | EEG | µV |
| Electrocardiogram | ECG | µV |
| Blood glucose | BG | mg/dL |
| Arterial systolic blood pressure | ABPSYS | MmHg |
| Arterial diastolic blood pressure | ABPDIAS | MmHg |
| Arterial average blood pressure | ABPMEAN | MmHg |
| Electrocardiogram | HR | 1/min |
| Heart rate | PAPSYS | mmHg |
| Pulmonary systolic artery pressure | PAPDIAS | mmHg |
| Pulmonary diastolic artery pressure | T | Celsius |
| Body temperature | SPO2 | % |
| Oxygen saturation | RESP | 1/min |
| Respiratory rate | ECG | µV |

1. Electroencephalogram (EEG): EEG is not included in the BioAura because it cannot be conveniently captured at this time. The current method for capturing EEG requires the user to wear a cap. Moreover, its capture devices cannot be miniaturized further because electrodes need to form a minimum diameter to be noise-robust. It should be understood that this biostream could be included once suitable detection mechanisms become available.

2. Electrocardiogram (ECG): We have excluded ECG from the list of our Biostreams because the feature extraction mechanism required for it is much more compute-intensive on a smartphone relative to the simple feature extraction mechanism that we employ for the nine chosen Biostreams. This would drain the smartphone battery faster. For example, even performing a low-complexity feature extraction on one minute of ECG signals requires at least 400× more operations than performing a simple statistical feature extraction, e.g., averaging, on the respiratory rate values [ECGC]. If we try to avoid the preprocessing (i.e., feature extraction) on the smartphone and just transmit the ECG signals to the authentication system, this would also entail significant energy consumption since ECG waveforms contain at least 200 samples/s.

3. Blood glucose (BG): BG is excluded because currently the devices that measure BG require active user involvement (i.e., the user provides one drop of blood). It should be understood that this biostream could be included once suitable, e.g., non-invasive, detection mechanisms become available.

In this example nine Biostreams are used to form the BioAura in the prototype implementation. It should be understood that the CABA system need not necessarily be limited to these nine. As other compact WMSs become available in the future, they could also be made part of the BioAura. Note that, unlike biometrics, we do not expect any one Biostream to have high discriminatory power. High discriminatory power arises only through an ensemble of Biostreams, i.e., the BioAura, as we will see later.

Scope of Applications

In this section, we describe the possible applications of CABA. The concept of continuous authentication based on BioAura can potentially be used to protect (i) personal computing devices and servers, (ii) software applications, and (iii) restricted areas. Next, we conceptually describe how CABA can be implemented and utilized to protect each domain.

Personal Computing Devices and Servers

There is a need to protect computing devices (e.g., personal computers) and servers against unauthorized access for two main reasons. First, such systems may store sensitive information (e.g., personal information, credit card numbers and the like). Second, they can be used to access other restricted systems and resources. Computing devices (e.g., personal computers, laptops, tablets, and smart phones) or servers can employ two different approaches to exploit the BioAura approach: (i) they can use their own computing resources to implement a stand-alone version of the system, or (ii) they can simply use decisions made by a portion of the system implemented on a trusted server. Both approaches are explained in detail below.

Example 1

Figure 3:
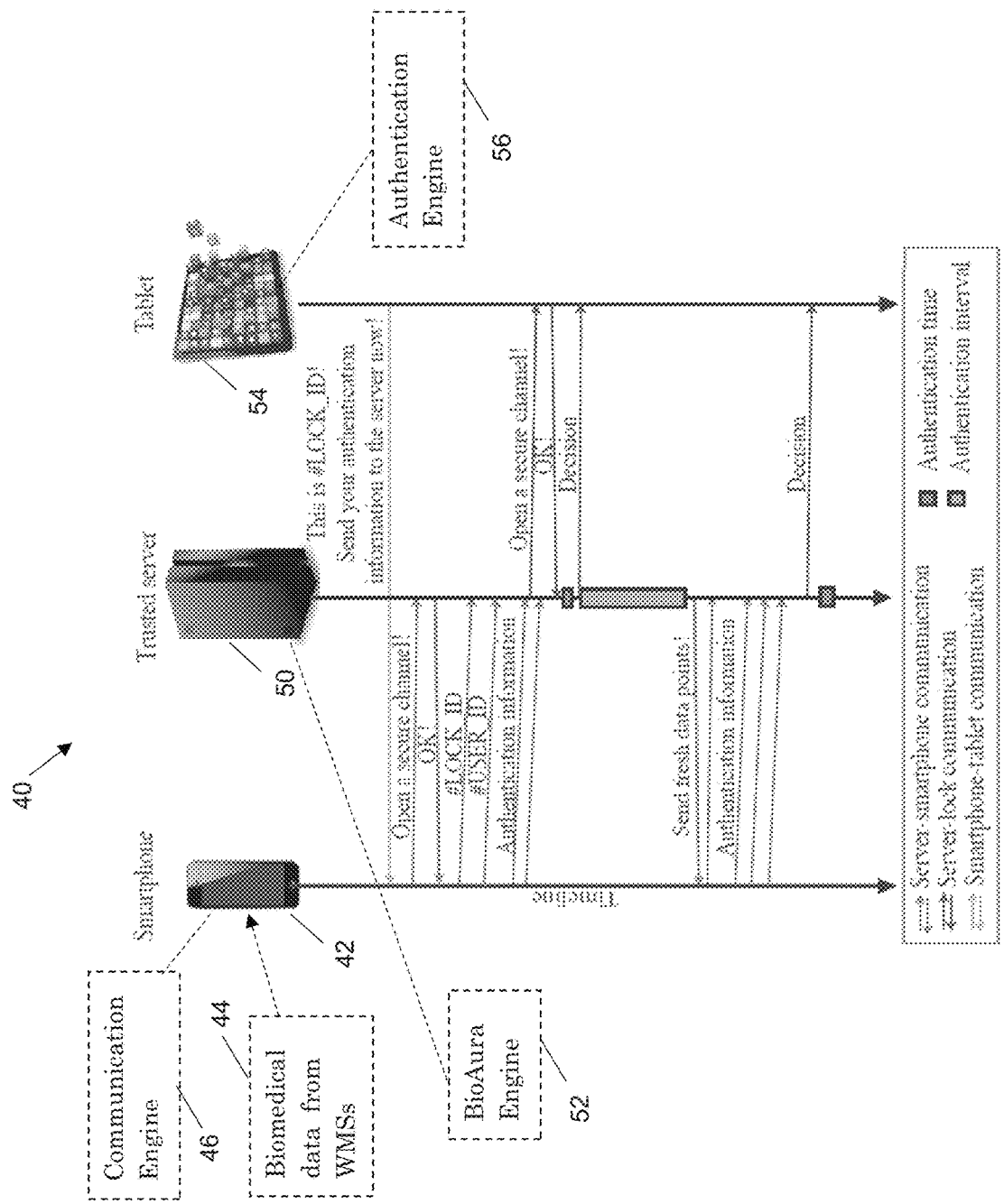
FIG. 3 is a block diagram of a CABA system configured for authentication of a tablet.

FIG. 3 is a block diagram of a CABA system configured for authentication of a tablet 54. The system includes a smart phone 42 (base station) and a trusted server 50 (back end server). It should be understood that the smart phone 42 and trusted server 50 both include at least one processor. As disclosed above, biomedical data is collected from the WMSs 44 by the smartphone 42. The smartphone 42 also includes a communication engine 46 configured to retrieve the biomedical data from the receive buffers contained in the smart phone. The communication engine 46 may perform some signal processing on the biomedical data or simply re-transmit the raw biomedical data to the trusted server 50. The trusted server 50 is configured with receive buffers to store the biomedical data and a BioAura Engine 52 for processing the biomedical data from the receive buffers in the trusted server.

Suppose tablet 54 wants to authenticate its user using BioAura. The tablet may be unable to dedicate its limited memory/energy resources to support the whole authentication process. In such a scenario, it can use decisions made by the trusted server 50 running the BioAura engine 52. When the user tries to unlock the tablet 54, the authentication engine 56 informs communication engine 46 in the user's smartphone. The communication engine 46 asks the trusted server to open a secure communication channel. The communication engine 46 then sends the information required for specifying the device that needs to be unlocked (e.g., the tablet ID) along with the information that needs to be processed to authenticate the user (e.g., the user ID and a preprocessed frame of data points from his BioAura) to the BioAura engine 52 on the trusted server. The trusted server then authenticates the user and sends this decision to the authentication engine 56 on the tablet 54. After initial login, the trusted server 50 demands fresh data points at certain intervals.

Example 2

Figure 4:
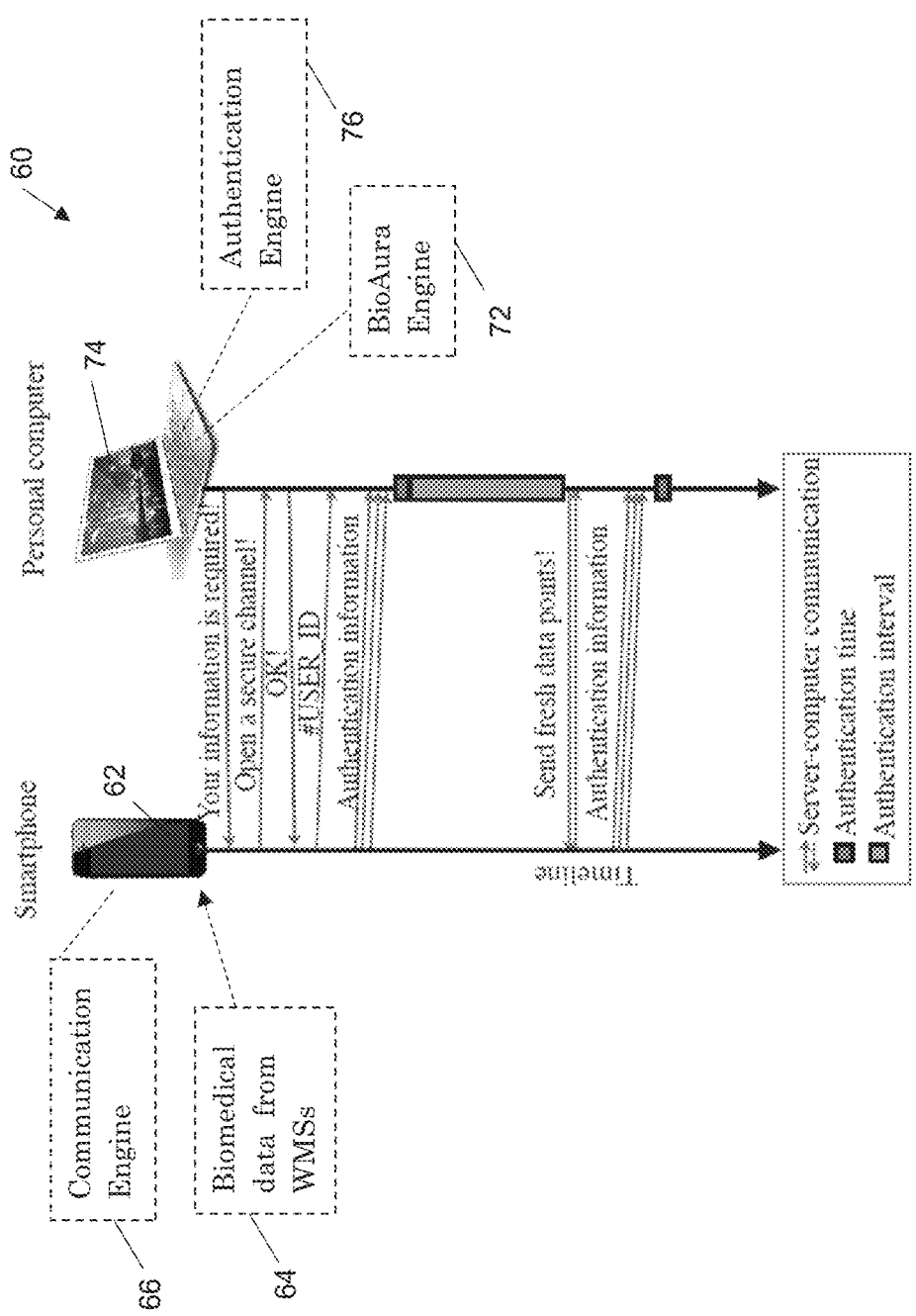
FIG. 4 is a block diagram of a CABA system configured for authentication of a personal computer.
Figure 5:
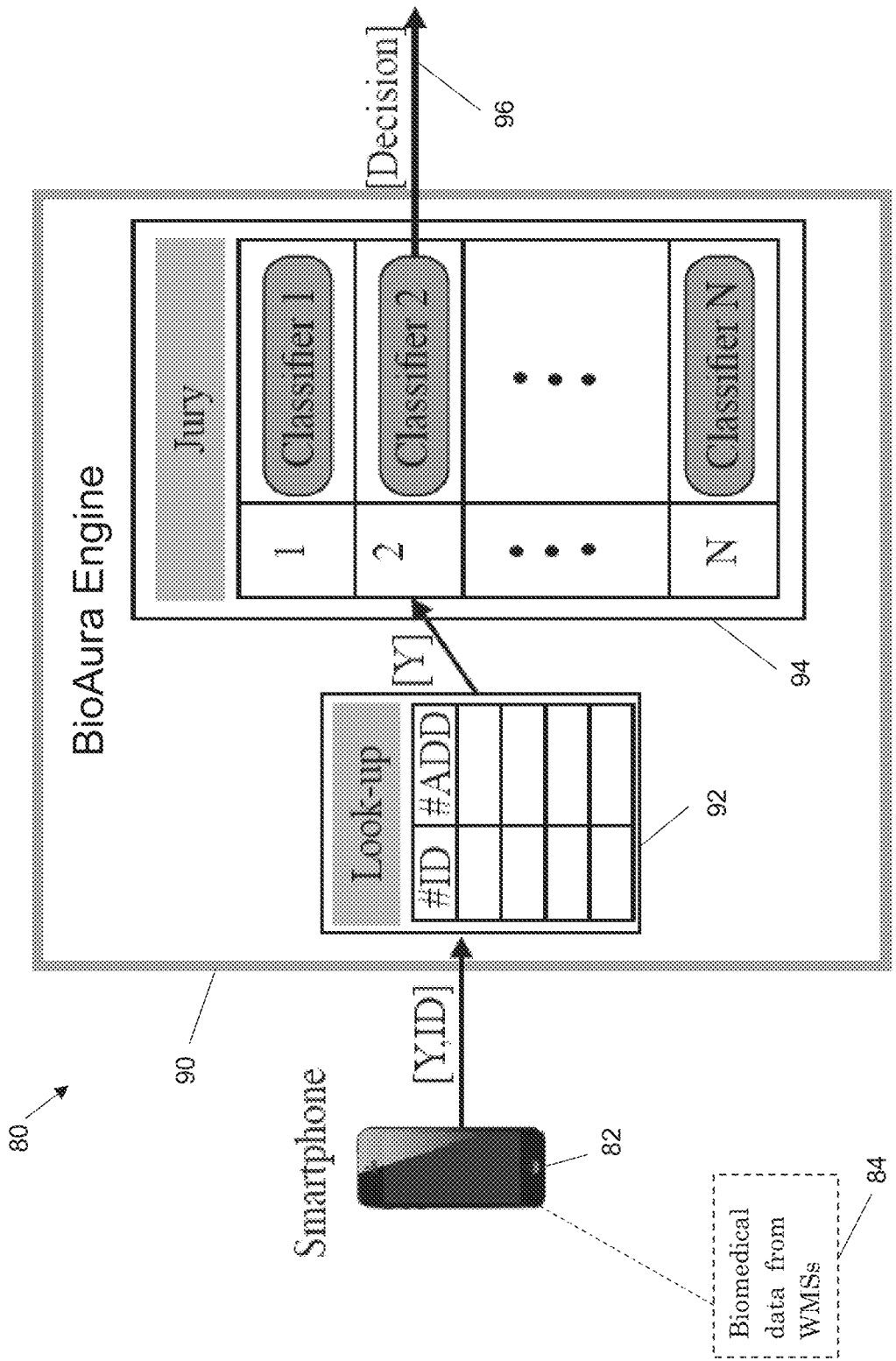
FIG. 5 is a block diagram that illustrates how the CABA system works when the user requests authentication.

FIG. 4 is a block diagram of a CABA system configured for authentication of a personal computer 74. Suppose the user wants to login to his personal computer 74. In this case, the personal computer 74 has enough computational power and energy capacity to implement a stand-alone version of the BioAura engine 72. This case is similar to the one in Example 1, except that there is no need for a trusted server.

When the user tries to unlock the personal computer 74, the authentication engine 76 informs communication engine 66 in the user's smartphone 62 and establishes a secure communication channel. The communication engine 66 then sends the information required to authenticate the user (e.g., a preprocessed frame of data points from his BioAura) to the BioAura engine 72 on the personal computer 74. The BioAura engine 72 then authenticates the user and sends this decision to the authentication engine 76. After initial login, the BioAura engine 72 demands fresh data points at certain intervals.

Restricted Areas

Authentication systems are also used to control access to restricted physical areas (e.g., buildings, rooms, and datacenters). Typically, the electronic access device that controls the entrance (e.g., a smart lock) would not have enough computation power to use a stand-alone version of the CABA system. Hence, in such cases, the CABA system can be implemented on a trusted server, and authentication decisions are determined on the trusted server and then transmitted to the electronic access device. This case is similar to the one depicted in FIG. 3 with the tablet replaced by the lock.

Prototype Implementation

The BioAura engine includes a machine learning model that uses the biomedical data from each of WMSs to validate or identify users. In this section, we describe the learning and decision making phases of BioAura engine.

Learning Phase

In the learning phase, the BioAura engine is given a training dataset. The model is built using a supervised learning approach (i.e., a machine learning approach in which the model is built based on labeled training data points).

Generally, the amount of information needed to build a model varies from one application to another. The number of training data points needed was evaluated to examine how much information should be sent to the BioAura engine to build a reliable and accurate model. Each data point in the training set is nine-dimensional (as shown in the lower 9 entries in Table III) and includes the average values of successive measurements of a Biostream over a one-minute timeframe. The value of each dimension is represented using half-precision floating-point format that requires two bytes of storage. Therefore, if the smartphone needs to transmit data points extracted over a one-hour period, it only needs to send 1080 bytes of data to the authentication system over this period.

In order to maintain reliability, the BioAura engine should train a new model based on fresh medical data obtained at certain intervals. In other words, the BioAura engine should update the model regularly to ensure that the model maintains accuracy and can distinguish legitimate users from impostors. The frequency of model update (i.e., how frequently the BioAura engine should repeat the learning phase) depends on several factors, such as required accuracy and learning time. Experimental results indicate that when the BioAura engine re-trains the model every four hours, it achieves the good accuracy and the learning time is only a few minutes. Learning can be done transparently to the user. In other words, the BioAura engine can re-train the model while the user continues to be authenticated. For example, suppose the learning phase takes five minutes each time and is repeated every four hours (i.e., each model is used for four hours). The BioAura engine can start re-training to generate a new model after 3 hours and 55 minutes, and be ready with it after four hours have elapsed.

Real-Time Decision Making Phase

In this phase, the BioAura engine makes decisions using the already-trained model. In a continuous authentication scenario, the BioAura engine should verify the user's identity at certain intervals. The frequency of authentication depends on several factors, such as the required level of security and the amount of information required for one authentication. In our prototype implementation, we assume that the BioAura engine re-authenticates the user every minute based on a given nine-dimensional data point Y that contains the average values of the chosen Biostreams over a specified time interval. When the user approaches the authentication system and requests authentication, the smartphone performs a simple computation on the already-gathered Biostreams and provides Y. Therefore, unlike most previously-proposed continuous authentication systems (e.g., keyboard/mouse-based mechanisms) that require the user to wait while they collect authentication information, the BioAura engine obtains the required information almost instantaneously because the information has already been gathered and stored on the smartphone for the purpose of health monitoring.

FIG. 4 is a block diagram that illustrates how the CABA system 80 works when the user requests authentication. In a single verification attempt:

1. The smartphone 82 preprocesses one minute of Biostreams collected from WMSs 84. Then, it transmits the preprocessed information (Y) along with user ID to the BioAura Engine 90. The BioAura engine includes a look up stage 92 and a classifier 94.

2. The Look-up stage 92 sends Y to the appropriate stage of the classifier 94 (Jury stage) based on the given user ID.

3. The dedicated classifier processes Y and generates a binary decision 96 (accept or reject).

Look-Up Stage

This stage forwards the nine-dimensional vector Y (in this example) provided by the smartphone to the appropriate classifier based on the given user ID. In order to provide a fast search mechanism to find the appropriate classifier, this stage can be implemented using a hash table that associates user IDs with pointers to the classifiers.

Jury Stage

In this example, the Jury stage includes N binary classifiers, where N is the number of people who need to be authenticated. The i-th classifier is trained to only accept the data point Y that is extracted by the i-th user's smartphone from the user's BioAura. The training set of the i-th classifier consists of the i-th user's data points labeled as "accept" and others' data points labeled as "reject".

Two well-known binary classification methods were used: Support Vector Machine (SVM) and Adaptive Boosting (AdaBoost). Next, each method is described.

SVM: The basic concept in an SVM is to find a hyperplane that separates the n-dimensional data into two classes. However, since the data points in the dataset are not usually linearly separable, SVMs introduce the concept of kernel trick that projects the points into a higher-dimensional space, where they are linearly separable. When no prior knowledge about the dataset is available, SVMs usually demonstrate promising results and generalize well.

AdaBoost: The idea behind AdaBoost is to build a highly accurate classifier by combining many weak classifiers. Choosing appropriate weak classifiers is a significant consideration in AdaBoost. The most commonly used weak learning methods for implementing AdaBoost-based classifiers are decision stumps (also called one-node tree) and decision trees.

Experimental Setup and Metrics

In this section, we first describe the parameters and dataset used in some experiments. Then, the accuracy and scalability metrics used to evaluate the proposed authentication system are discussed.

Experimental Parameters and Dataset

In the next section, the parameters that were set in an experimental setup are discussed and the dataset is described Parameters The following five key parameters were used in connection with the experimental setup.

Dataset length (L): This is the duration of Biostreams measurements, i.e., the number of hours of information we have for each person in our data set. In our experiments, we used 14 hours of data for each individual (i.e., L=14 h).

Dataset dimension (n): This is the number of Biostreams that form the BioAura of an individual. In our setup, we have included nine Biostreams for each person (i.e., n=9).

Dataset size (N): This is the number of people in the dataset (N=37 in our experiments).

Testing window size (TEW): This represents the duration of biomedical measurements (expressed in hours) for each individual used to evaluate the accuracy of the trained model in the real-time decision making phase. For example, if TEW is 1 hour, it means we have included 60 data points in our testing set, where each point is a nine-dimensional vector consisting of the average values of successive measurements of the nine Biostreams over a one-minute timeframe. We vary the value of TEW in our experiments to evaluate its impact on the performance of CABA.

Training window size (TRW): This represents the duration of the biomedical measurements (expressed in hours) for each individual that we used for training the model in the learning phase. We vary TRW in our experiments to study its impact on the model's accuracy.

Dataset

In order to evaluate the accuracy of CABA, we have used a freely available multi-parameter dataset, called MIMIC-II. MIMIC-II has been extensively used in the medical and biomedical fields. It includes several anonymized high-resolution vital sign trends, waveforms, and sampled biomedical signals for many individuals. We chose the 37 medical records in MIMIC-II that provide values for all of the required Biostreams for at least 14 hours.

Accuracy Metrics

Next, we define five metrics that we used for analyzing the accuracy of the proposed authentication system. The first three are traditionally used for evaluating authentication mechanisms. We define two more to evaluate accuracy in the context of continuous authentication.

False acceptance rate (FAR): This is the ratio of falsely accepted unauthorized users to the total number of invalid requests made by impostors trying to access the system. In the context of continuous authentication, we use the notation $FAR_{t=TEW}$ to denote FAR under TEW.

False rejection rate (FRR): This refers to the ratio of falsely rejected requests to the total number of valid requests made by legitimate users trying to access the system. We use the notation $FRR_{t=TEW}$ to denote FRR under TEW.

Equal error rate (EER): This is the point where FAR equals FRR. Reporting only FRR or FAR does not provide the complete picture because there is a trade-off between the two since we can make one of them low by letting the other one become high. Therefore, we mainly use EER (instead of FRR or FAR) for reporting CABA's accuracy. As before, we use the notation $EER_{t=TEW}$ to denote EER under TEW.

Figure 6:
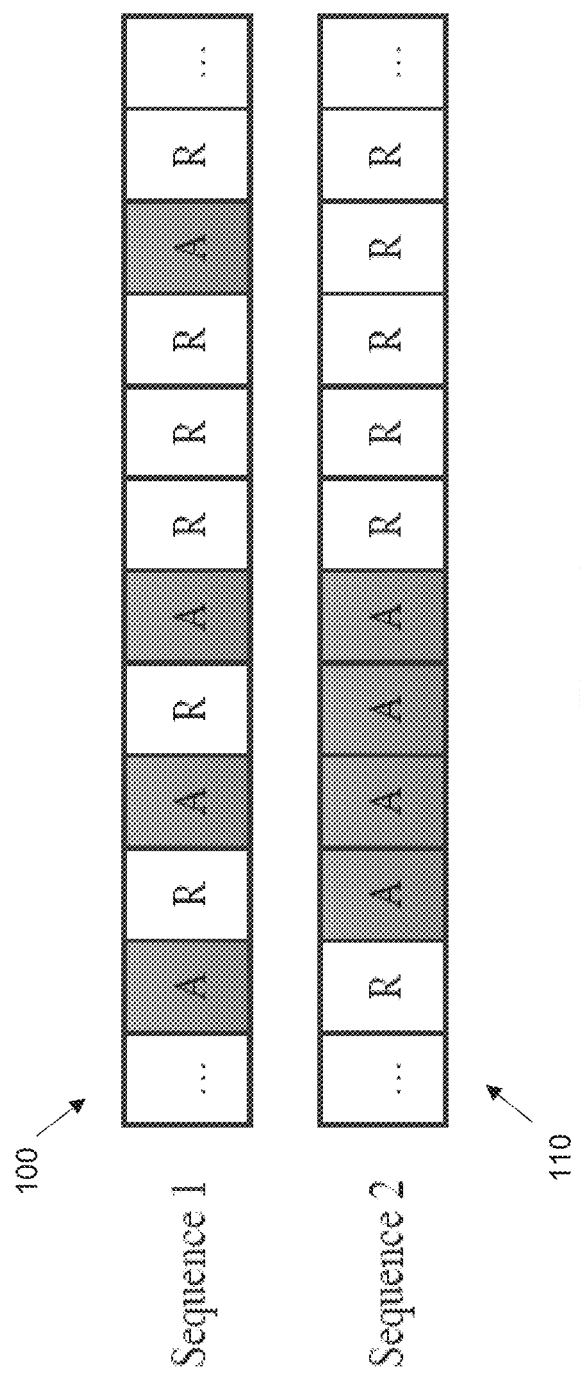
FIG. 6 shows two possible output sequences over a ten-minute authentication timeframe when an impostor is trying to get authenticated.

False acceptance worst-case interval (FAW): The output of the authentication system in a time period T is a sequence of accept/reject decisions. As an example, FIG. 6 shows two possible output sequences over a ten-minute authentication timeframe when an impostor is trying to get authenticated. In both sequences, the number of falsely accepted requests is the same. However, in a continuous authentication scenario, the second sequence would be considered worse since the impostor can use the system over a four-minute timeframe without being detected, whereas in the first case the impostor can only use the system over a one-minute timeframe. We define FAW as the longest time interval (expressed in minutes for CABA) over which an impostor can be falsely accepted as a legitimate user. In the example of FIG. 6, FAW is one minute and four minutes for the first and second cases, respectively.

False rejection worst-case interval (FRW): Analogously to FAW, we define FRW as the longest time interval (expressed in minutes) over which a legitimate user might be falsely rejected and marked as an impostor.

Scalability Metrics

In order to analyze the scalability of the proposed method, we consider two metrics: time complexity and space complexity, using the well-known O notation. We express them as a function of the number N of the people in the dataset.

Evaluating the CABA Prototype

In this section, we evaluate CABA from both the accuracy and scalability perspectives.

Authentication Accuracy

In order to examine the accuracy of the authentication system, we have implemented a prototype of CABA in Matlab.

The accuracy of a model is generally evaluated using a set of data points that is different from the set used in constructing the model. Thus, in order to train and test a model, the dataset can be divided into two parts: training and test sets. Cross-validation is often used for this purpose. The classical K-fold cross-validation refers to the case in which the dataset is divided into K folds (K−1 folds for training and one fold for testing), under the assumption that potential dependencies across observations are time-independent. However, K-fold cross-validation cannot be used to estimate the performance of a system that processes a time series (i.e., a sequence of data points consisting of successive measurements) because potential local dependencies across observations in a time series define a structure in the data that will be ignored by cross-validation. Thus, as disclosed herein, instead of using traditional cross-validation, we have designed several experimental scenarios for evaluating the accuracy of the authentication system. We describe these scenarios next.

1. Baseline:

In the baseline scenario, we break the available dataset into two equal parts (i.e., TEW=TRW=7 h). We use the first half of the dataset (the first seven hours) of each individual to train the model and the second half to test it. We use all the Biostreams (i.e., n=9) to train and test our system. We use two classification methods: SVM and AdaBoost. In the case of SVM, we use two kernels [linear and radial basis function (RBF)]. In the case of AdaBoost, we consider decision stumps (one-node tree) and decision trees with 5, 10, 15, and 20 nodes as weak classifiers. We run 40 iterations for all Adaboost-based classifiers since we determined experimentally that the training error becomes zero within these many iterations and testing error becomes minimum. The value of $EER_{t=7\ h}$ is reported in Table IV for all classifiers. AdaBoost with a tree size of 15 (i.e., with 15 nodes in the tree) has the minimum value of $EER_{t=7\ h}$. Increasing tree size usually improves the accuracy of Adaboost-based classifiers. However, using larger trees leads to more complex models, which are more susceptible to overfitting. This can be seen when we move from a tree size of 15 to 20.

TABLE IV

| Type of classifier | Specification | $EER_{t=7\ h}$ (%) |
|---|---|---|
| SVM | Kernel = Linear | 3.0 |
|  | Kernel = RBF | 2.6 |
| AdaBoost | Tree size = 1 | 3.1 |
|  | Tree size = 5 | 2.9 |
|  | Tree size = 10 | 2.9 |
|  | Tree size = 15 | 2.4 |
|  | Tree size = 20 | 2.5 |

Table V summarizes FAW and FRW for all classification schemes. Consider RBF SVM as an example. Its FAW is 4 minutes, which suggests that, in the worst case, an impostor can deceive the authentication system for a 4-minute timeframe. Its FRW is 3 minutes, which suggests that, in the worst case, a legitimate user is falsely rejected for a stretch of 3 minutes.

TABLE V

| Type of classifier | Specification | F AW (min) | F RW (min) |
|---|---|---|---|
| SVM | Kernel = Linear | 4 | 3 |
|  | Kernel = RBF | 4 | 3 |
| AdaBoost | Tree size = 1 | 5 | 3 |
|  | Tree size = 5 | 4 | 3 |
|  | Tree size = 10 | 4 | 3 |
|  | Tree size = 15 | 4 | 3 |
|  | Tree size = 20 | 4 | 4 |

2. Biased $FAR_t/FRR_t$:

Even though it is easier to compare authentication methods based on their $EER_t$, we may want to minimize $FAR_t$ in highly-secure environments in order to ensure that an impostor is not authorized or minimize $FRR_t$ to enhance user convenience. A low $FAR_t$ indicates a high security level and a low $FRR_t$ ensures user convenience. In this experimental scenario, we use the same parameters that are used in the baseline. However, false acceptance and false rejection are penalized differently. We consider two cases: (i) try to make $FAR_t$ close to zero ($FAR_{t=7\ h}$<0.1%) and measure $FRR_t$, and (ii) try to make $FRR_t$ close to zero ($FRR_{t=7\ h}$<0.1%) and measure $FAR_t$. Tables W and VII summarize the results for these two cases. Based on Table VI, the CABA system can be seen to ensure impostors are not accepted, but at the cost of an increase in FRR. Based on Table VII, the CABA system can be seen to not negatively impact user convenience (i.e., not falsely reject the user), while rejecting impostors in more than 90% of the cases.

TABLE VI

| Type of classifier | Specification | F RR(%) |
|---|---|---|
| SVM | Kernel = Linear | 10.2 |
|  | Kernel = RBF | 9.6 |
| AdaBoost | Tree size = 1 | 10.0 |
|  | Tree size = 5 | 9.7 |
|  | Tree size = 10 | 8.7 |
|  | Tree size = 15 | 8.4 |
|  | Tree size = 20 | 8.9 |

TABLE VII

| Type of classifier | Specification | F AR(%) |
|---|---|---|
| SVM | Kernel = Linear | 8.9 |
|  | Kernel = RBF | 7.6 |
| AdaBoost | Tree size = 1 | 10.7 |
|  | Tree size = 5 | 9.2 |
|  | Tree size = 15 | 7.8 |
|  | Tree size = 15 | 7.6 |
|  | Tree size = 20 | 8.2 |

Figure 7:
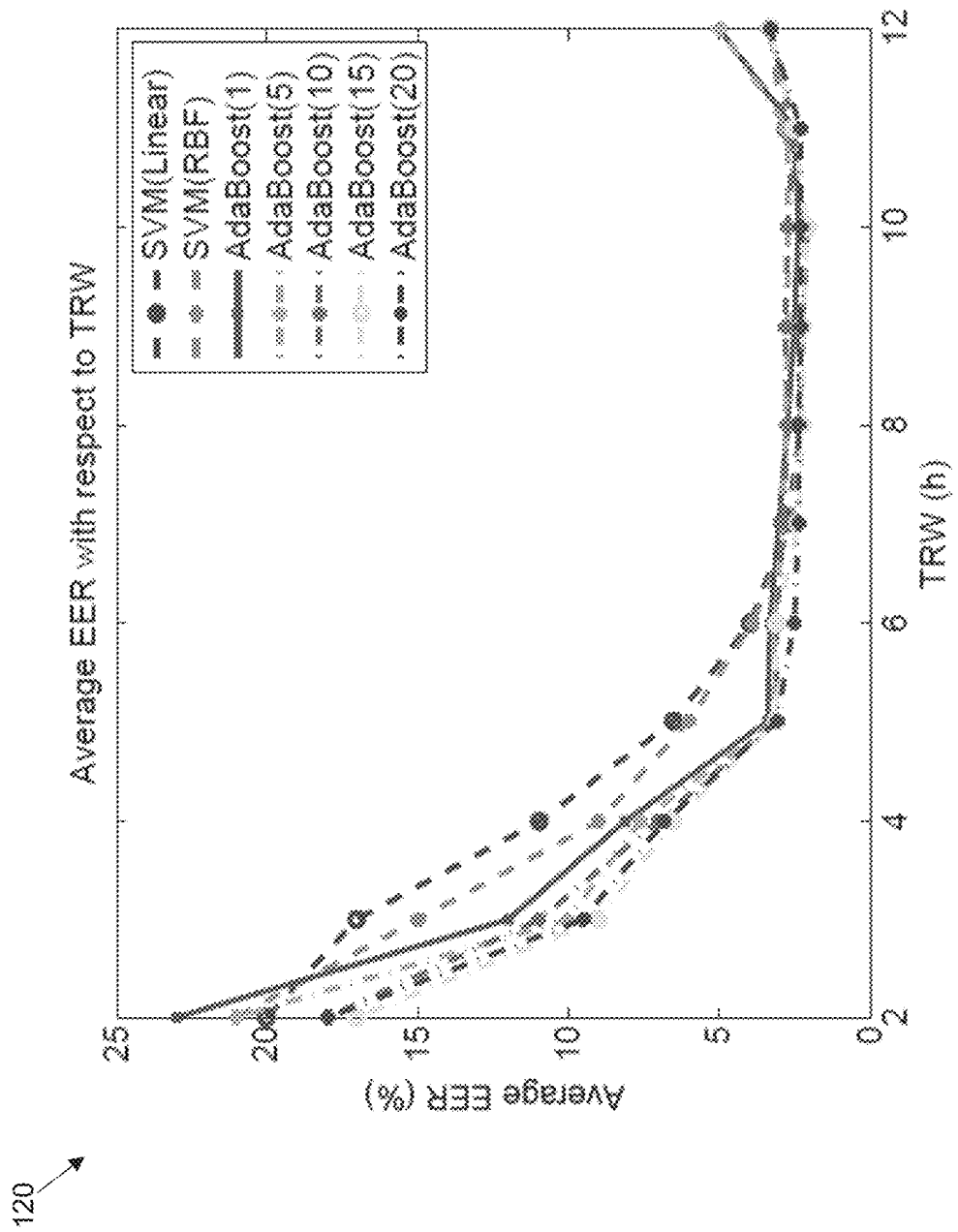
FIG. 7 shows the average $EER_t$ for different classifiers with respect to TRW.

3. Variable Window Size:

As mentioned earlier, we set the training and testing window sizes to 7 h in the baseline. Here, we change the size of the training and testing windows such that TRW=2, 3, . . . , 12 h and TEW+TRW=14 h. FIG. 7 shows the average $EER_t$ for different classifiers with respect to TRW. For all classifiers, as we increase TRW from 2 h to 6 h, $EER_t$ decreases drastically, then it remains almost constant until TRW reaches 11 h. Above this TRW, EER starts increasing for two possible reasons. First, the model may become overfitted. Second, the number of test points may be inadequate.

Figure 8:
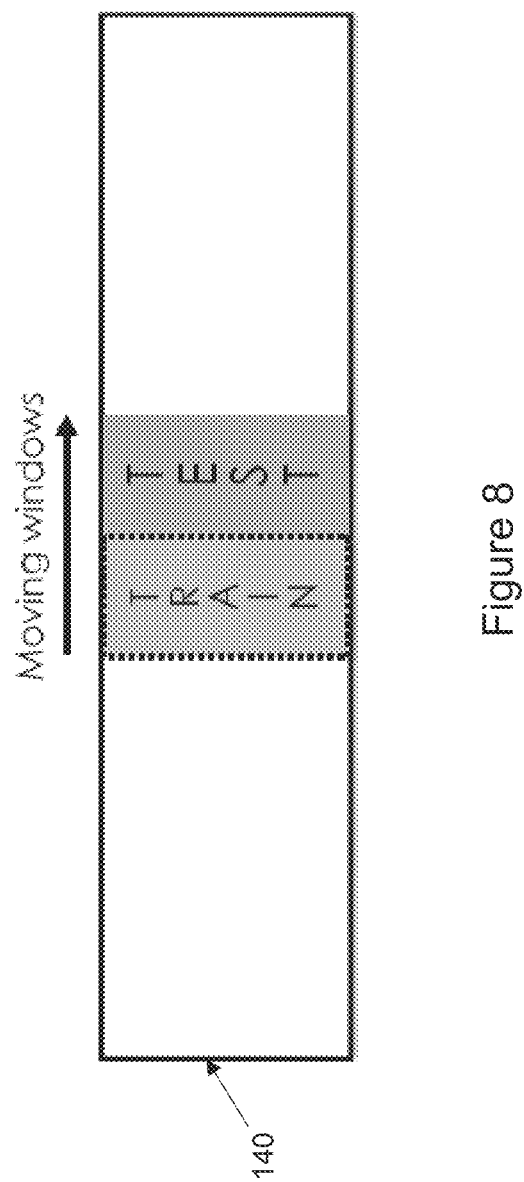
FIG. 8 shows moving training windows.

4. Moving Training Window:

In this scenario, the training window moves behind the testing window (FIG. 8). We consider TEW=TRW=1, 2, . . . , 7 h. Our experimental results demonstrate that this verification scheme provides the best result for TEW=TRW=4 h, for which the average $EER_t$ is 1.9% and the classification method is AdaBoost with a tree size of 15 nodes. This suggests that we can achieve the best accuracy for TRW=4 h, under the assumption that the trained model is valid for the next four hours.

Figure 9:
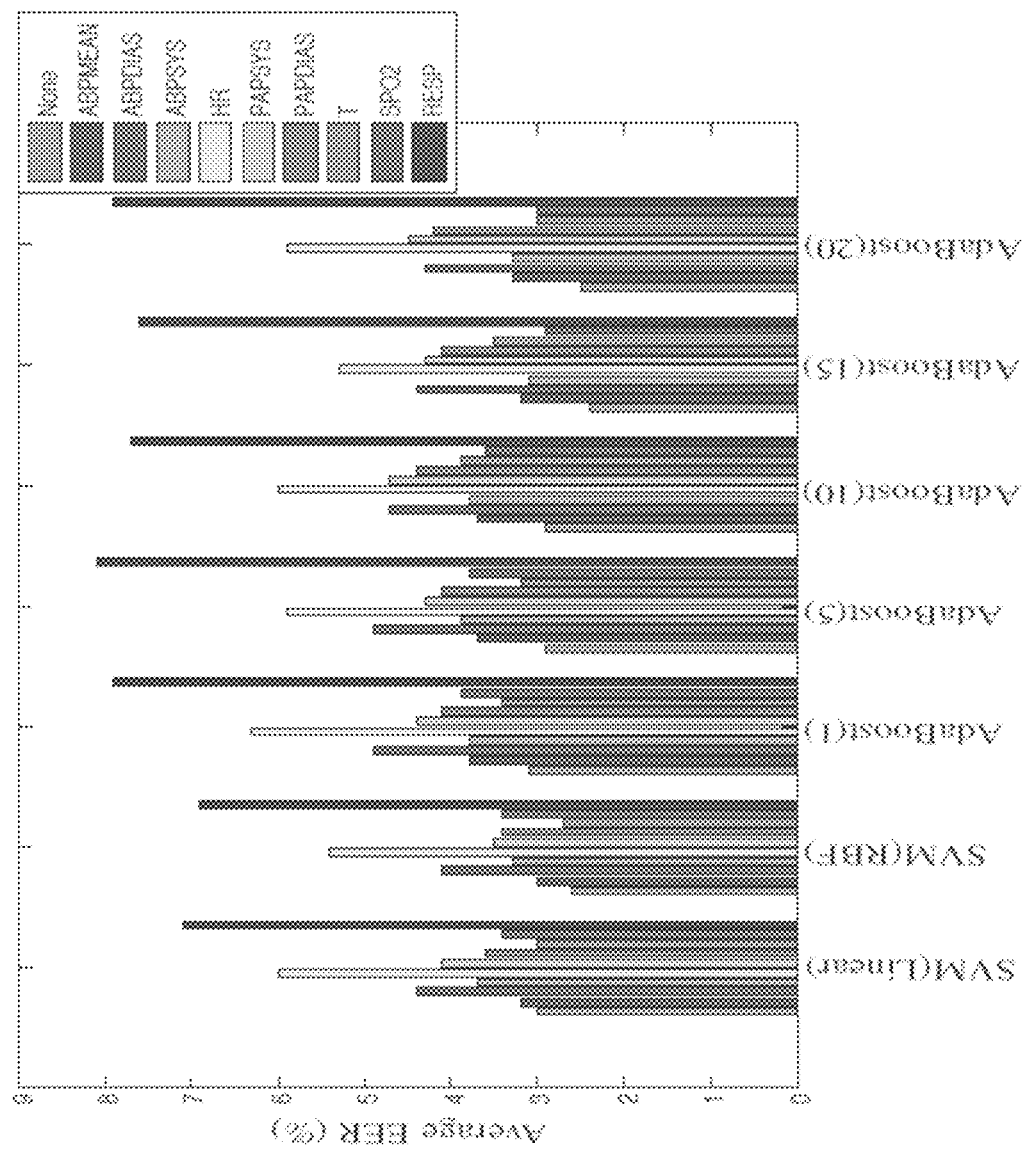
FIG. 9 is a graph showing how $EER_{t=7\,h}$ changes when we drop different Biostreams.

5. Reducing the Number of Biostreams:

We also examine what happens if we drop a Biostream. Traditionally, feature reduction is used to remove redundant or irrelevant features from the data set before commencing on the training process in order to decrease unnecessary computational cost. However, in our scenario, the main purpose of feature reduction is to examine how each feature affects accuracy. If CABA can provide an acceptable accuracy (target accuracy level) with fewer features, fewer WMSs would be required. We dropped one feature at a time and computed $EER_{t=7\ h}$ of the system. All other configurations are kept the same as in the baseline. FIG. 9 illustrates how $EER_{t=7\ h}$ changes when we drop different Biostreams. It indicates that the most and least important Biostreams are respiratory rate and body temperature, respectively.

CABA Scalability

We discuss below the worst-case time and space complexities of CABA.

Time Complexity

As discussed earlier, CABA can be implemented in such a manner that the time required by the learning phase is hidden from the user's perspective. Hence, we focus on the time complexity of the decision making process. We found that the required time for processing an authentication request for N=37 was on the order of a few milliseconds for all classification methods, when CABA was implemented on a MacBook Pro (2.3 GHz Intel Core i7 processor with 8 GB memory). This suggests that CABA can re-authenticate the user very quickly.

When a person requests authentication by providing his ID and feature vector Y, the Look-up stage forwards Y to one and only one classifier in the Jury stage based on the given user ID. Then, the classifier's decision is the final decision of the authentication system. Hence, in order to analyze the time complexity of a single decision making process, we need to consider the time complexity of the Look-up stage, and one classifier in the Jury stage, as follows:

Look-up stage: If the Look-up stage is implemented using a hash table that associates user IDs with pointers to classifiers, then its search operation (finding the location of the classifier associated with the user ID) can be performed in $O(1)$ time.

One classifier in the Jury stage: The time complexity of the classifier varies from one classification algorithm to another. The time complexities of AdaBoost classifiers and the SVM classifier with a linear kernel do not depend on N (i.e., they have time complexity of $O(1)$). The time complexity of SVM with an RBF kernel is $O(n_{SV})$, where $n_{SV}$ is the number of support vectors. Theoretically, $n_{SV}$ grows linearly with a linear increase in N. Thus, the SVM classifier with an RBF kernel has a time complexity of $O(N)$.

Hence, the overall time complexity of decision making is just $O(1)$ for AdaBoost classifiers and the SVM classifier with a linear kernel, and $O(N)$ for the SVM classifier with an RBF kernel.

Space Complexity

We first examine how much memory is required for storing the authentication system. Then, we discuss how the amount of memory required to store the two stages (Look-up and Jury) increases with N.

The amount of memory required for storing the Look-up stage in our prototype, where N=37, was less than 1 kB. The amount of memory required for storing a single classifier in the Jury stage varies from tens of bytes (for SVM with a linear kernel) to a few kB (for AdaBoost with a tree size of 20). Therefore, the total amount of memory allocated to the authentication system is less than 1 MB.

Thus, we examine the space complexity as a function of N.

Look-up stage: If the Look-up stage is implemented using a hash table, its space complexity is $O(N)$.

Jury stage: The space complexity of a single classifier in the Jury stage depends on the type of classifier. The space complexities of AdaBoost classifiers and the SVM classifier with a linear kernel do not depend on N (i.e., they have space complexity of $O(1)$). However, the space complexity of the SVM with an RBF kernel is $O(N)$. Since the number of classifiers in the Jury stage increases linearly with N, its space complexity is $O(N)$ (when an AdaBoost classifier or SVM classifier with a linear kernel is used) or $O(N^2)$ (when the SVM classifier with the RBF kernel is employed).

To sum up, the space complexity of the authentication system is either $O(N)$ (for AdaBoost classifiers and the SVM classifier with a linear kernel) or $O(N^2)$ (for the SVM classifier with the RBF kernel)

Supporting Identification in the CABA System

Figure 10:
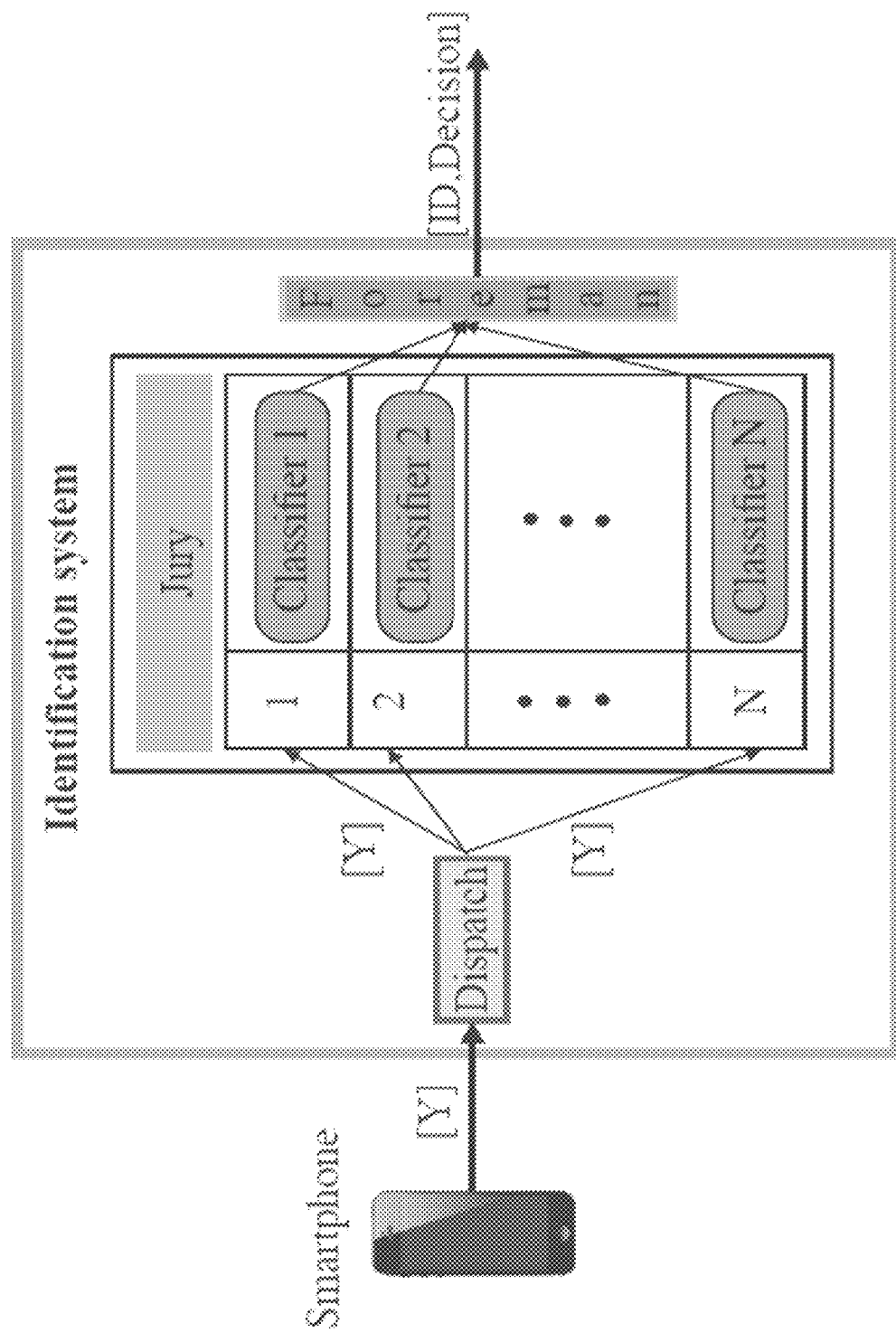
FIG. 10 is a block diagram showing how a CABA system can identify a user.

The majority of continuous authentication systems only support continuous verification in which the user provides a user ID and the system checks if the user is the person he purports to be. In this section, we describe how CABA can be modified to also identify the user from a database of users by processing feature vector Y provided by the smartphone. A continuous authentication system that also supports identification works as follows. When a legitimate user sends his first request to the system, the system first identifies the user and outputs a user ID. Then, the system assumes that the current user is the one who has been identified and continuously verifies the user identity. FIG. 10 is a block diagram showing how a CABA system can identify a user. Each identification scenario includes several steps:

1. The smartphone preprocesses a one-minute timeframe of data points that are collected from the user's BioAura. Then, it transmits the preprocessed data (Y) to the authentication system.

2. Unlike the verification scenario, in which Y is sent to only one classifier, in the identification scenario, the Dispatch stage forwards Y to all classifiers in the Jury stage.

3. All classifiers process Y simultaneously, and output N binary decisions.

4. The decisions of all classifiers in the Jury stage are sent to the Foreman stage. The Foreman stage either indicates that the user is not in the database, or concludes that he is, in which case it returns his user ID. This stage can be implemented in different ways. For example, the Foreman Algorithm shows a simple pseudo-code for this stage. The algorithm receives all outputs from the Jury stage and outputs the user ID if there is only one classifier whose output is an accept decision. Otherwise, it indicates no match.

Real-Time Adaptive Authorization

In this section, we first define the concept of authorization. Then, we propose a real-time adaptive authorization (RAA) scheme, which uses the decisions from CABA to provide an extremely flexible access control model. The RAA concept is not limited to CABA. It provides an adjustable access control model for any authorization system that authorizes the user based on decisions of a continuous authentication system.

Authorization is defined as the process of establishing if the user, who is already authenticated, is allowed access to a resource, system, or area.

Traditional authorization schemes grant a specific access level to the authenticated user based on his user ID. However, the fact that continuous authentication mechanisms have a non-zero FRR implies that such a simple scheme may unintentionally block a legitimate access when the authentication system fails to recognize a valid user for a short period of time. Consider a scenario in which a continuous authentication system is used to protect a personal laptop from unauthorized users. The authentication system first authenticates the user. Then, the authorization scheme specifies the user's access level based on the user ID. However, the laptop may log out the user when the authentication scheme falsely rejects him. RAA schemes can be used to alleviate user inconvenience caused by false reject decisions. They continuously adjust the user's access level based on the last decision of the authentication system. Next, we propose a RAA scheme that can be used with a continuous authentication system. A Foreman Algorithm is disclosed in U.S. provisional application 62/291,877, filed Feb. 5, 2016, which is incorporated herein in its entirety.

Trust Level-Based RAA

A trust level-based RAA adaptively changes the user's access level based on a parameter called trust level (TRL). TRL is a recently-suggested parameter that represents how much we trust a user based on previous decisions of the continuous authentication system. TRL has a value between 0 and 100, where a higher number indicates a higher level of trust. The initial value of TRL is 100 when the user is authenticated and authorized for the first time. The value of TRL is continuously updated using a trust update procedure after each decision making step. A simple trust update procedure may be to just increase (decrease) the TRL by a constant step after each accept (reject) decision. Trust update procedure shows the pseudo-code for such an approach. We need to set two parameters: $W_{Accept}$ and $W_{Reject}$. The values $W_{Accept}$ and $W_{Reject}$ should be chosen such that the TRL value becomes 0 as soon as we detect the presence of an impostor and becomes 100 when we confidently verify that the user is legitimate. Consider AdaBoost classification with a tree size of 15 nodes that yields FRW=3. This indicates that the authentication system may falsely reject three consecutive requests of a legitimate user in the worst case. Therefore, if the RAA scheme gets at least four consecutive reject decisions from the authentication system, it becomes confident that the user is an impostor (TRL=0). Hence, we can set $W_{Reject}$ for this classifier as follows:

$$W_{Reject} = \frac{-100}{FRW+1} = \frac{-100}{4} = -25.$$

FAW=4 for the above-mentioned classification method, which indicates that in the worst case, an impostor may be falsely accepted as a legitimate user in four successive trials. Therefore, if the authentication system outputs five consecutive accent decisions. TRL should become 100. Thus, we can set $W_{Accept}$ as follows:

$$W_{Accept} = \frac{+100}{FAW+1} = \frac{+100}{5} = +20.$$

We can set different threshold values for different applications. For example, we can set the threshold value to 100 for accessing email and financial accounts to ensure that the user can access such accounts only when the system is confident that the user is legitimate. However, for less sensitive applications (e.g., simple web surfing), a lower level of trust might be sufficient. A Trust update procedure is also disclosed in U.S. provisional application 62/291,877, filed Feb. 5, 2016, which is incorporated herein in its entirety.

Potential Threats and Countermeasures

In this section, we briefly describe possible attacks against CABA and potential security threats that can be exploited by attackers to bypass CABA. For each attack, we also suggest possible countermeasures.

1. Eavesdropping: This is defined as the act of covertly listening to confidential conversation of others, which, in our context, can be done by intercepting the communication between two devices using appropriate equipment (e.g., HackRF). Eavesdropping can occur when unencrypted information is transmitted over an untrusted channel.

Countermeasures: The most effective and well-known defense against eavesdropping is encryption. For example, the transmitted message can be encrypted using Advanced Encryption Standard [AESBOOK]. However, implementing a strong encryption in WMSs may not be possible in the current state of the technology since they have limited energy and memory capacity. Fortunately, eavesdropping does not pose a direct threat to the authentication system. In other words, it is possible to design the authentication system assuming that eavesdropping does occur on the communication between the WMSs and the smartphone. In this case, CABA would require that the data be sent from a smartphone that is previously registered in the system to ensure that the attacker is not able to capture the medical information and send the captured information to CABA using another smartphone. The smartphone can send its unique ID over a secure communication link to CABA before transmitting the biomedical information.

2. Phishing: This is an attack that attempts to fool the user into submitting his confidential or private information (e.g., username, password, email address, and phone number) to an untrusted server or device. A potential phishing attack against CABA may be launched as follows. The attacker might attempt to fool the user's smartphone by sending a counterfeit request that asks the smartphone to send its authentication-related information to the attacker's server.

Countermeasures: The most effective way to address phishing attacks is to use a digital certificate (i.e., an electronic document that allows a device to exchange information securely using the public key infrastructure). The certificate carries information about the key and its owner. In CABA, the server's digital certificate can be examined by the smartphone to ensure that the server that asks for the information is the trusted server.

3. Replay attack: In a replay attack, an attacker records the data, packets, and user's credentials, which are transmitted between two devices (e.g., a WMS and the smartphone), and exploits them for a malicious purpose. In a replay attack against the authentication system, the attacker attempts to impersonate a legitimate user in order to bypass the authentication procedure and gain full access to the protected device, application, or area. Unlike the attacks based on eavesdropping, in a replay attack, the attacker does not need to interpret the packets. In fact, he can even record encrypted packets and retransmit them in order to bypass the system.

Countermeasures: An encrypted timestamp (i.e., a sequence of encrypted information identifying when the transmission occurred) can be utilized to enable the authentication system to check that the packets were not previously recorded. Moreover, the packet should include a field that contains the encrypted information (e.g., a hashed device ID), which can be used in the authentication system to uniquely specify the sender of the packets and check if the sender is known and trusted.

4. Poisoning attack: In a poisoning attack, the attacker changes the final learning model by adding precisely-selected invalid data points to the training dataset. In CABA, the attacker might threaten the integrity of the machine learning algorithm by using an untrusted WMS that aims to add malicious data points to the training set.

Countermeasures: We describe two main types of countermeasures against poisoning attacks.

Outlier detection: One of the common goals of defenses against poisoning attacks is to reduce the effect of invalid data points on the final result. In a machine learning method, such invalid data points are considered outliers in the training dataset. Mozaffari-Kermani et al. have presented and evaluated several countermeasures against poisoning attacks.

Digitally-signed medical information: A digital signature can be used to check the authenticity of the information. A digital signature is a mathematical method for demonstrating the authenticity of a transmitted message. Thus, it provides the means to the recipient to check if the message is created by a legitimate sender. The WMSs and the smartphone can digitally sign the biomedical information before transmitting it.

Further disclosure is contained in U.S. provisional application 62/291,877, filed Feb. 5, 2016, which is incorporated herein in its entirety. All references that are cited in the appendix of U.S. provisional application 62/291,877 and the references section of the appendix are also incorporated herein in their entirety. It should be understood that many variations are possible based on the disclosure herein. Although features and elements are described above in particular combinations, each feature or element can be used alone without the other features and elements or in various combinations with or without other features and elements. The digital processing techniques disclosed herein may be partially implemented in a computer program, software, or firmware incorporated in a computer-readable (non-transitory) storage medium for execution by a general-purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

Suitable processors include, by way of example, a general-purpose processor, a special purpose processor, a conventional processor, a digital signal processor (DSP), a plurality of microprocessors, one or more microprocessors in association with a DSP core, a controller, a microcontroller, Application-Specific Integrated Circuits (ASICs), Field-Programmable Gate Arrays (FPGAs) circuits, any other type of integrated circuit (IC), and/or a state machine.

What is claimed is:

1. A system for continuous authentication of a user of an electronic device for use with a plurality of wireless wearable medical sensors (WMSs) and a wireless base station configured to receive a biomedical data stream (biostream) from each of the plurality of WMSs, the biostream from a single WMS lacking enough discriminatory power to distinguish the user, the system comprising:

a BioAura engine located on a server, the server having one or more receive buffers configured to store a preprocessed plurality of biostreams, the BioAura engine being configured to:

transmit the preprocessed plurality of biostreams to a classifier particular to a user of the electronic device via a look up stage; and generate an authentication output to authenticate the user's access to the electronic device based on whether the preprocessed plurality of biostreams matches a trained model of the user's plurality of biostreams via the classifier particular to the user, the trained model based on an initial training dataset comprising multi-dimensional data points containing average values of successive measurements of the retrieved biostreams over a specified time interval, the trained model being periodically updated with subsequent training datasets each comprising multi-dimensional data points containing average values of successive measurements of the retrieved biostreams over a specified time interval;

the wireless base station having a communication engine configured to:

retrieve the biostream from each WMS;

preprocess the retrieved biostreams by creating a multi-dimensional data point containing average values of the retrieved biostreams over a specified time interval; and transmit the preprocessed plurality of biostreams to the server.

2. The system of claim 1 wherein the retrieved biostreams comprise at least two of the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2), and Respiratory rate (RESP).

3. The system of claim 1 wherein the retrieved biostreams comprise at least three of the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2), and Respiratory rate (RESP).

4. The system of claim 1 wherein the retrieved biostreams comprise the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2), and Respiratory rate (RESP).

5. The system of claim 1 wherein the retrieved biostreams are selected based on a target accuracy level.

6. The system of claim 1 wherein the BioAura engine is operated continuously, generating the authentication output on a periodic or an a-periodic basis.

7. The system of claim 1 wherein preprocessing the retrieved biostreams reduces the bandwidth needed to transmit the preprocessed plurality of biostreams to the server.

8. The system of claim 1 wherein the wireless base station is a smartphone.

9. The system of claim 1 wherein the electronic device is at least one of a tablet and a smart lock.

10. The system of claim 1 wherein the classifier is implemented using one of Support Vector Machine (SVM) and Adaptive Boosting (AdaBoost).

11. A system for continuous authentication of a user of a computing device for use with a plurality of wireless wearable medical sensors (WMSs) and a wireless base station configured to receive a biomedical data stream (biostream) from each of the plurality of WMSs, the biostream from a single WMS lacking enough discriminatory power to distinguish the user, the system comprising:

a BioAura engine located on the computing device, the computing device having one or more receive buffers configured to store a plurality of biostreams, the BioAura engine being configured to:

transmit the preprocessed plurality of biostreams to a classifier particular to a user of the computing device via a look up stage; and generate an authentication output to authenticate the user's access to the computing device based on whether the preprocessed plurality of biostreams matches a trained model of the user's plurality of biostreams via the classifier particular to the user, the trained model based on an initial training dataset comprising multi-dimensional data points containing average values of successive measurements of the retrieved biostreams over a specified time interval, the trained model being periodically updated with subsequent training datasets each comprising multi-dimensional data points containing average values of successive measurements of the retrieved biostreams over a specified time interval;

the wireless base station having a communication engine configured to:

retrieve the biostream from each WMS;

preprocess the retrieved biostreams by creating a multi-dimensional data point containing average values of the retrieved biostreams over a specified time interval; and transmit the preprocessed plurality of biostreams to the computing device.

12. The system of claim 11 wherein the retrieved biostreams comprise at least two of the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2), and Respiratory rate (RESP).

13. The system of claim 11 wherein the retrieved biostreams comprise at least three of the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2), and Respiratory rate (RESP).

14. The system of claim 11 wherein the retrieved biostreams comprise the following biostreams: Arterial systolic blood pressure (ABPSYS), Arterial diastolic blood pressure (ABPDIAS), Arterial average blood pressure (ABPMEAN), Heart rate (HR), Pulmonary systolic artery pressure (PAPSYS), Pulmonary diastolic artery pressure (PAPDIAS), Body temperature (T), Oxygen saturation (SPO2), and Respiratory rate (RESP).

15. The system of claim 11 wherein the retrieved biostreams are selected based on a target accuracy level.

16. The system of claim 11 wherein preprocessing the retrieved biostreams reduces the bandwidth needed to transmit the preprocessed plurality of biostreams to the computing device.

17. The system of claim 11 wherein the computing device is a personal computer.

18. The system of claim 11 wherein the BioAura engine is operated continuously, generating the authentication output on a periodic or an a-periodic basis.

19. The system of claim 11 wherein the classifier is implemented using one of Support Vector Machine (SVM) and Adaptive Boosting (AdaBoost).

20. A system for continuous authentication of a user of an electronic device for use with a plurality of wireless wearable medical sensors (WMSs) and a wireless base station configured to receive a biomedical data stream (biostream) from each of the plurality of WMSs, the biostream from a single WMS lacking enough discriminatory power to distinguish the user, the system comprising:

a BioAura engine located on a server, the BioAura engine being configured to:

retrieve the biostreams from the wireless base station;

preprocess the retrieved biostreams by creating a multi-dimensional data point containing average values of the retrieved biostreams over a specified time interval;

transmit the preprocessed plurality of biostreams to a classifier particular to a user of the electronic device via a look up stage; and generate an authentication output to authenticate the user's access to the electronic device based on whether the preprocessed plurality of biostreams matches a trained model of the user's plurality of biostreams via the classifier particular to the user, the trained model based on an initial training dataset comprising multi-dimensional data points containing average values of successive measurements of the retrieved biostreams over a specified time interval, the trained model being periodically updated with subsequent training datasets each comprising multi-dimensional data points containing average values of successive measurements of the retrieved biostreams over a specified time interval.

* * * * *